US012685459B2

(12) United States Patent (10) Patent No.: US 12,685,459 B2
Eum (45) Date of Patent: Jul. 21, 2026

(54) VOLATILE ORGANIC COMPOUND CAPTURING DEVICE

(71) Applicant: Spiracheck Limited, Middlesex (GB)

(72) Inventor: Jay Eum, Irvine, CA (US)

(73) Assignee: Spiracheck Limited, Middlesex (GB)

( * ) Notice: Subject to any disclaimer, the term of this patent is extended or adjusted under 35 U.S.C. 154(b) by 659 days.

(21) Appl. No.: 18/010,923

(22) PCT Filed: Jun. 24, 2021

(86) PCT No.: PCT/GB2021/051605
§ 371 (c)(1),
(2) Date: Dec. 16, 2022

(87) PCT Pub. No.: WO2021/260383
PCT Pub. Date: Dec. 30, 2021

(65) Prior Publication Data

US 2023/0293042 A1 Sep. 21, 2023

Related U.S. Application Data

(60) Provisional application No. 63/044,920, filed on Jun. 26, 2020.

(51) Int. Cl.
*A61B 5/097* (2006.01)
*A61B 5/00* (2006.01)
*A61B 5/08* (2006.01)
(52) U.S. Cl.
CPC ............. *A61B 5/097* (2013.01); *A61B 5/082* (2013.01); *A61B 5/742* (2013.01)

(58) Field of Classification Search
CPC ....... A61B 5/082; A61B 5/0836; A61B 5/097; A61B 5/7475
USPC ....................................................... 600/532
See application file for complete search history.

(56) References Cited

U.S. PATENT DOCUMENTS

| | | | |
|---|---|---|---|
| 9,357,961 B2 | 6/2016 | Arefieg | |
| 2009/0318823 A1* | 12/2009 | Christman | A61B 5/097 600/532 |
| 2013/0305808 A1* | 11/2013 | Yoo | G01N 33/4972 73/23.3 |
| 2014/0276100 A1* | 9/2014 | Satterfield | A61B 5/7271 600/476 |
| 2015/0005657 A1 | 1/2015 | Nijsen et al. | |
| 2017/0332951 A1* | 11/2017 | Ahmad | G16H 50/20 |
| 2018/0153439 A1* | 6/2018 | Miller | G01N 1/22 |

(Continued)

FOREIGN PATENT DOCUMENTS

| | | | | |
|---|---|---|---|---|
| JP | 2003/307473 A | 10/2003 | | |
| WO | WO-2004028366 A1 * | 4/2004 | | A61B 5/097 |

(Continued)

OTHER PUBLICATIONS

International Search Report and Written Opinion for PCT Application No. PCT/GB2021/051605 mailed on Dec. 13, 2021, 24 pp.

*Primary Examiner* — Mark Edwards
(74) *Attorney, Agent, or Firm* — Dickinson Wright PLLC

(57) ABSTRACT

Disclosed herein include systems, devices, and methods for capturing compounds, such as volatile organic compounds, in gaseous samples onto capturing tubes, such as thermal desorption tubes, for subsequent analysis, such as disease diagnosis (e.g., cancer diagnosis).

16 Claims, 12 Drawing Sheets

(56) References Cited

U.S. PATENT DOCUMENTS

| | | | | |
|---|---|---|---|---|
| 2019/0009249 A1* | 1/2019 | Gao | .......................... | B01J 20/12 |
| 2019/0257757 A1 | 8/2019 | Thomas et al. | | |
| 2020/0319100 A1* | 10/2020 | Beydaghyan | ............ | G01N 1/40 |

FOREIGN PATENT DOCUMENTS

| | | | |
|---|---|---|---|
| WO | WO 2013/118098 A1 | 8/2013 | |
| WO | WO 2014/130376 A1 | 8/2014 | |

* cited by examiner

Machine

Adsorption tube

Bag

```
                VODCA
```

```
           Detatch VOC Bag

Press SEL to Cont...
```

```
         Purging System
          Please Wait...

Timer:10        Tube#:1
```

```
         File No. is: 1043

Press Next to Cont...
```

```
    Flow:200 Time:060
    INC: up DEC: down
    NEXT: next field
    Press SEL when done
``` machine          Adsorption tube          bag

```
    Breathe into the Bag

Sampling will start in
         10 seconds
```

```
   Time: 056    Batt: AC
   Flow: 206    Temp: 23.9
   Co2:  445    RH: 55
```

*FIG. 6*

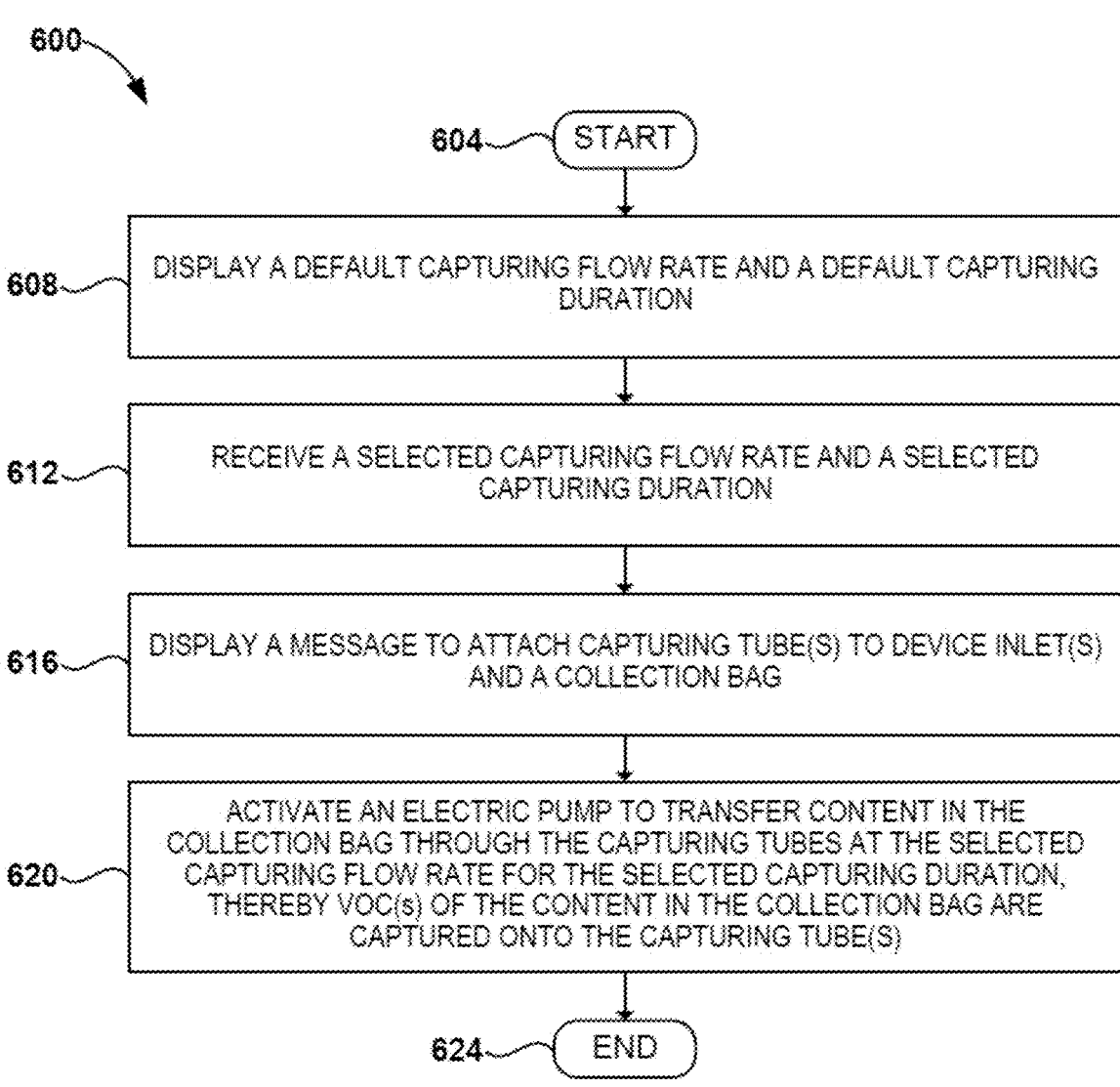

600

604 — START

608 — DISPLAY A DEFAULT CAPTURING FLOW RATE AND A DEFAULT CAPTURING DURATION

612 — RECEIVE A SELECTED CAPTURING FLOW RATE AND A SELECTED CAPTURING DURATION

616 — DISPLAY A MESSAGE TO ATTACH CAPTURING TUBE(S) TO DEVICE INLET(S) AND A COLLECTION BAG

620 — ACTIVATE AN ELECTRIC PUMP TO TRANSFER CONTENT IN THE COLLECTION BAG THROUGH THE CAPTURING TUBES AT THE SELECTED CAPTURING FLOW RATE FOR THE SELECTED CAPTURING DURATION, THEREBY VOC(s) OF THE CONTENT IN THE COLLECTION BAG ARE CAPTURED ONTO THE CAPTURING TUBE(S)

624 — END

VOLATILE ORGANIC COMPOUND CAPTURING DEVICE

BACKGROUND

The present disclosure relates generally to the field of capturing compounds, for example capturing volatile organic compounds.

FIELD

Description of the Related Art

Compounds, such as volatile organic compounds (VOCs), can be analyzed for various purposes. For example, VOCs can be used as diagnostic and prognostic markers in assays for health screening and disease detection (e.g., cancer detection). There is a need for capturing compounds efficiently for accurate analysis of the captured compounds.

SUMMARY

In a first aspect of the invention, there is provided a device for capturing one or more compounds in a gaseous sample comprising: one or more device inlets for attaching one or more gaseous sample capturing tubes; a device outlet; a pump connected to the one or more device inlets for drawing a gaseous sample, or a portion thereof, through the one or more device inlets and expelling the content of the gaseous sample, or a portion thereof, through the device outlet; one or more sensors connected to the device inlets, the pump, and/or the device outlet via one or more air tubes; a user interface; non-transitory memory configured to store executable instructions; and a microcontroller in communication with the pump, the one or more sensors, the user interface, and the non-transitory memory, the microcontroller programmed by the executable instructions to perform: receiving a selected gaseous sample capturing flow rate and a selected gaseous sample capturing duration; receiving an input to proceed; and activating the pump to transfer the content in the gaseous sample collection container, or a portion thereof, through the one or more gaseous sample capturing tubes, into the device via the one or more device inlets and out of the device via the device outlet, at the selected gaseous sample capturing flow rate for the selected gaseous sample capturing duration, thereby one or more compounds of the content in the gaseous sample collection container, or a portion thereof, collected are captured onto the one or more gaseous sample capturing tubes.

In some embodiments, the pump is an electric pump. In some embodiments, the user interface comprises a display. In some embodiments, the gaseous sample collection container is a gaseous sample collection bag. In some embodiments, the microcontroller is further programmed by the executable instructions to perform: causing the display to show a default gaseous sample capturing flow rate and a default gaseous sample capturing duration. In some embodiments, the microcontroller is further programmed by the executable instructions to perform: causing the display to show a message to attach one or more gaseous sample capturing tubes to the one or more device inlets and a gaseous sample collection bag. In some embodiments, the microcontroller is further programmed by the executable instructions to perform: causing the display to show a message requesting a gaseous sample to be collected through a bag inlet of the gaseous sample collection bag for a gaseous sample collection duration. In some embodiments, the microcontroller is further programmed by the executable instructions to perform: showing on the display a countdown of the gaseous sample collection duration remaining.

Disclosed herein include embodiments of a device for capturing one or more compounds in a gaseous sample. In some embodiments, the device comprises: one or more device inlets for attaching one or more gaseous sample capturing tubes. The device can comprise: a device outlet. The device can comprise: an electric pump connected to the one or more device inlets for drawing a gaseous sample, or a portion thereof, through the one or more device inlets and expelling the content of the gaseous sample, or a portion thereof, through the device outlet. The device can comprise: one or more sensors connected to the device inlets, the electric pump, and/or the device outlet via one or more air tubes. The device can include a display. The device can include: non-transitory memory configured to store executable instructions. The device can include: a microcontroller in communication with the electric pump, the one or more sensors, the display, and the non-transitory memory. The microcontroller can be programmed by the executable instructions to perform: causing the display to show a default gaseous sample capturing flow rate and a default gaseous sample capturing duration. The microcontroller can be programmed by the executable instructions to perform: receiving a selected gaseous sample capturing flow rate and a selected gaseous sample capturing duration. The microcontroller can be programmed by the executable instructions to perform: causing the display to show a message to attach one or more gaseous sample capturing tubes to the one or more device inlets and a gaseous sample collection bag. The microcontroller can be programmed by the executable instructions to perform: receiving an input to proceed. The microcontroller can be programmed by the executable instructions to perform: causing the display to show a message requesting a gaseous sample to be collected through a bag inlet of the gaseous sample collection bag for a gaseous sample collection duration. The microcontroller can be programmed by the executable instructions to perform: showing on the display a countdown of the gaseous sample collection duration remaining. The microcontroller can be programmed by the executable instructions to perform: activating the electric pump to transfer the content in the gaseous sample collection bag, or a portion thereof, through the one or more gaseous sample capturing tubes, into the device via the one or more device inlets and out of the device via the device outlet, at the selected gaseous sample capturing flow rate for the selected gaseous sample capturing duration, thereby one or more compounds of the content in the gaseous sample collection bag, or a portion thereof, collected are captured onto the one or more gaseous sample capturing tubes. In some embodiments, the one or more device inlets are identical. The one or more device inlets can be adjacent to each other.

In some embodiments, at least one of the one or more sensors is connected to the electric bump and the device outlet via at least one of the one or more air tubes. In some embodiments, at least one of the one or more sensors is connected to at least one of the one or more device inlets and the electric bump via at least one of the one or more air tubes.

In some embodiments, the microcontroller is programmed by the executable instructions to perform: generating sample identification information. The microcontroller can be programmed by the executable instructions to perform: causing the display to show sample identification information. The microcontroller can be programmed by the executable instructions to perform: receiving an input to proceed. In some embodiments, the microcontroller is programmed by the executable instructions to perform: causing the display to show a message requesting sample identification information. The microcontroller can be programmed by the executable instructions to perform: receiving the sample identification information.

In some embodiments, the microcontroller is programmed by the executable instructions to perform, when activating the electric pump to transfer the content in the gaseous sample collection bag through the one or more gaseous sample capturing tubes, receiving sensor information from the one or more sensors. The microcontroller can be programmed by the executable instructions to perform: showing on the display the sensor information, or a portion thereof. The microcontroller can be programmed by the executable instructions to perform: generating a linkage relationship of the sensor information and the sample identification information. The microcontroller can be programmed by the executable instructions to perform: storing the sensor information, or a portion thereof, the sample information, and/or the linkage relationship in the non-transitory memory and/or a removable memory. The microcontroller can be programmed by the executable instructions to perform: transmitting the sensor information, or a portion thereof, the sample information, and/or the linkage relationship to a computing device.

In some embodiments, two or more sensors of the one or more sensors are connected sequentially. In some embodiments, two or more sensors of the one or more sensors are connected in parallel. In some embodiments, each sensor of the one or more sensors is connected to another sensor of the one or more sensors. In some embodiments, each sensor of the one or more sensors other than a sensor connected to the electric pump and a sensor connected to the device outlet is connected to two sensors of the one or more sensors.

In some embodiments, the one or more sensors comprises a flow rate sensor, a temperature sensor, a pressure sensor, a carbon dioxide ($CO_2$) sensor, a volatile organic compound (VOC) sensor, a humidity sensor, or a combination thereof. A sensor connected to the electric pump can comprise a flow rate sensor.

In some embodiments, one or each of the one or more air tubes is rigid, semi-rigid, or elastic. In some embodiments, a material of one or each of the one of the air tubes is latex, rubber, silicone, or a combination thereof.

In some embodiments, the device comprises: one or more valves in communication with the microcontroller. Each of the one or more valves in an opened state can allow the gaseous sample to enter into the device via one or more of the one or more device inlets the valve controls. Each of the one or more valves in a closed state can prevent the gaseous sample from entering into the device via one or more of the one or more device inlets the valve controls. The one or more valves can be in the closed state when the microcontroller is programmed by the executable instructions to perform: causing the display to show the message requesting the gaseous sample to be collected through the bag inlet of the gaseous sample collection bag for the gaseous sample collection duration. In some embodiments, the one or more valves comprise one or more solenoid valves. Each of the one or more valves can be connected to a different device inlet of the one or more device inlets.

In some embodiments, the display comprises a dot matrix display. In some embodiments, the display comprises a touch screen display for receiving inputs. In some embodiments, the device comprising: one or more input keys for receiving inputs. The one or more input keys can comprise one or more membrane keys. In some embodiments, the device comprises: a battery connected to the microcontroller for powering the microcontroller. The device can comprise: a power circuit connected to the battery for charging the battery. The power circuit can be connected to the microcontroller for powering the microcontroller. The device can comprise: a power inlet connected to the power circuit for connecting the battery charging circuit to an external power source.

In some embodiments, causing the display to show the message to attach the one or more gaseous sample capturing tubes to the one or more device inlets and the gaseous sample collection bag comprises: causing the display to show the message to attach a first tube opening of each of one or more gaseous sample capturing tubes to a different device inlet of the one or more device inlets and attach a second tube opening of each of the one or more gaseous sample capturing tubes to a different bag outlet of one or more bag outlets of the gaseous sample collection bag.

In some embodiments, the microcontroller is programmed by the executable instructions to perform: causing the display to show a message for any gaseous sample capturing tube attached to the one or more device inlets to be detached from the one or more device inlets. The microcontroller can be programmed by the executable instructions to perform: receiving an input to proceed. The microcontroller can be programmed by the executable instructions to perform: activating the electric pump at a purging flow rate for a purging duration. The microcontroller can be programmed by the executable instructions to perform: showing on the display a countdown of the purging duration remaining.

In some embodiments, the default gaseous sample capturing flow rate is about 5 ml/minute to about 2000 ml/minute. The selected gaseous sample capturing flow rate can be about 5 ml/minute to about 2000 ml/minute. The purging flow rate can be about 5 ml/minute to about 2000 ml/minute.

In some embodiments, the default gaseous sample capturing duration is about 1 minute to about 5 minutes. The selected gaseous sample capturing duration can be about 1 minute to about 5 minutes. The purging duration can be about 10 seconds to 60 seconds. In some embodiments, the gaseous sample collection duration is about 5 seconds to 20 seconds.

In some embodiments, the volume of gaseous sample collected in the gaseous sample collection bag during the gaseous sample collection duration is expected to be about 2.5 liters. The volume of the gaseous sample collected in the gaseous sample collection bag can be about 2.5 liters. The volume of the gaseous sample collected in the gaseous sample collection bag that passes through the one or more gaseous sample capturing tubes can be about 2 liters.

In some embodiments, the gaseous sample comprises one or more volatile organic compounds (VOCs). One or more of the VOCs of the content in the gaseous sample collection bag, or a portion thereof, collected can be captured onto the one or more gaseous sample capturing tubes. In some embodiments, the gaseous sample comprises a breath sample of a subject. Causing the display to show the message requesting the gaseous sample to be collected through the bag inlet of the gaseous sample collection bag for the gaseous sample collection duration can comprise causing the display to show a message requesting a subject to breath into the bag inlet of the gaseous sample collection bag for the gaseous sample collection duration. In some embodiments, the gaseous sample comprises an air sample.

In some embodiments, each of the one or more gaseous sample capturing tubes comprises a first tube opening, for attaching to one of the one or more device inlets, and a second tube opening, for attaching to a bag outlet of one or more bag outlets of the gaseous sample collection bag. One, or each, of the one or more bag outlets can be perpendicular to the bag inlet. In some embodiments, the gaseous sample collection bag comprises a bag body. The bag inlet can comprise an inlet assembly comprising a threaded inlet pipe, an inlet sealing washer, and an inlet snap ring. The threaded inlet pipe can be attached to an inlet hole of the bag body by the inlet sealing washer and the inlet snap ring. Each of the bag outlets can comprise an outlet assembly comprising a threaded outlet pipe, an outlet sealing washer, and an outlet snap ring. The threaded outlet pipe can be attached to an outlet hole of the bag body by the outlet sealing washer and the outlet snap ring. The inlet assembly can comprise an inlet cap for preventing the gaseous sample to enter or exit the gaseous sample collection bag. The outlet assembly can comprise an outlet cap for preventing the gaseous sample to enter or exit the gaseous sample collection bag. In some embodiments, the one or more bag outlets are identical. The one or more bag outlets can be adjacent to each other. The one or more bag outlets and the bag inlet can be identical. In some embodiments, the one or more gaseous sample capturing tubes comprise one or more thermal desorption tubes.

Disclosed herein include embodiments of a system for capturing one or more compounds (e.g., volatile organic compounds (VOCs)) in a gaseous sample. In some embodiments, the system comprises: a device for capturing one or more compounds a gaseous sample of the present disclosure; and an external power source. The system can comprise: instructions for operating the device.

Disclosed herein include embodiments of a method for capturing volatile organic compounds (VOCs). In some embodiments, the method comprises using a device for capturing one or more compounds of a gaseous sample of the present disclosure or a system for capturing one or more compounds of a gaseous sample of the present disclosure.

Disclosed herein include embodiments of a method for capturing volatile organic compounds (VOCs). In some embodiments, the method comprises: displaying a default volatile organic compound (VOC) sample capturing flow rate and a default VOC capturing duration. The method can comprise: receiving a selected VOC capturing flow rate and a selected VOC capturing duration. The method can comprise: displaying a message to attach one or more VOC capturing tubes to one or more device inlets of a device for capturing VOC) and a VOC collection bag. The method can comprise: receiving an input to proceed. The method can comprise: activating an electric pump of the device to transfer the content in the VOC collection bag through the one or more VOC capturing tubes, into the device via the one or more device inlets and out of the device via a device outlet, at the selected capturing flow rate for the selected capturing duration, thereby one or more VOCs in the content in the VOC collection bag are captured onto the one or more VOC capturing tubes. In some embodiments, the content of the VOC collection bag comprises a breath sample collected from a subject or a patient. In some embodiments, the content of the VOC collection bag comprises an environmental VOC sample.

Disclosed herein include embodiments of a gaseous sample collection bag. In some embodiments, the gaseous sample collection bag comprises a bag body comprising an inlet hole and one or more outlet holes. The gaseous sample collection bag can comprise a bag inlet. The gaseous sample collection bag can comprise one or more bag outlets. The bag inlet can comprise an inlet assembly comprising a threaded inlet pipe, an inlet sealing washer, and an inlet snap ring. The threaded inlet pipe can be attached to the inlet hole of the bag body by the inlet sealing washer and the inlet snap ring. Each of the one or more bag outlets can comprise an outlet assembly comprising a threaded outlet pipe, an outlet sealing washer, and an outlet snap ring. The threaded outlet pipe can be attached to one of the one or more outlet holes of the bag body by the outlet sealing washer and the outlet snap ring.

In some embodiments, the inlet assembly comprises an inlet cap for preventing the gaseous sample to enter or exit the gaseous sample collection bag. The outlet assembly can comprise an outlet cap for preventing the gaseous sample to enter or exit the gaseous sample collection bag. The one or more bag outlets can be identical. The one or more bag outlets can be next to each other. The one or more bag outlets and the bag inlet can be identical. In some embodiments, one, or each, of the one or more outlets holes and/or the inlet is on an edge, or are adjacent to an edge, of the bag body. One, or each, of the one or more outlets and/or the inlet can be on a diagonal, or adjacent to a diagonal of the bag body. In some embodiments, one, or each, of the one or more bag outlets is perpendicular, or approximately perpendicular, to the bag inlet. One, or each, of the one or more bag outlets and the bag inlet can be on different surfaces of the bag body. One, or each, of the one or more outlets and the inlet can be on an identical surface of the bag body.

In some embodiments, the bag body is rectangular or square in shape when deflated. The bag body comprises a sheet folded. In some embodiments, the bag body is sealed (e.g., heat sealed) on three sides. The bag body can be sealed (e.g., heat sealed) on all sides except one side. One, or each, of the sides of the bag body that is heat sealed can be impermeable to one or more volatile organic compounds. In some embodiments, a material of the bag body comprises high-density polyethylene (HDPE), low-density polyethylene (LDPE), and/or linear low-density polyethylene (LLDPE). A material of the bag body can be impermeable to one or more volatile organic compounds.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 6 is a flow diagram showing an exemplary method of capturing volatile organic compounds.

DETAILED DESCRIPTION

Figure 1A:
FIGS. 1A-1D show an exemplary compound capturing device and associated accessories, including exemplary sample capturing tubes and sample collection bag.
Figure 1B:
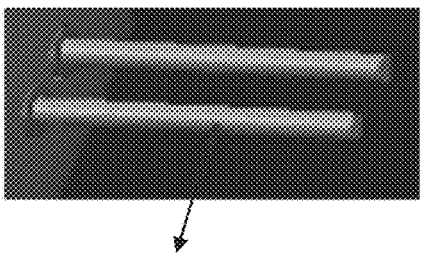
Figure 1C:
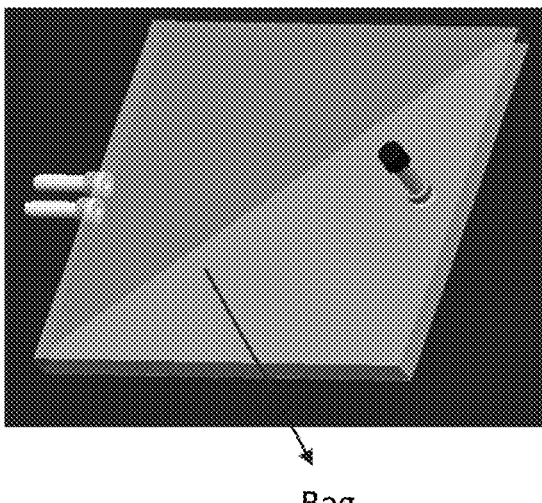
Figure 1D:
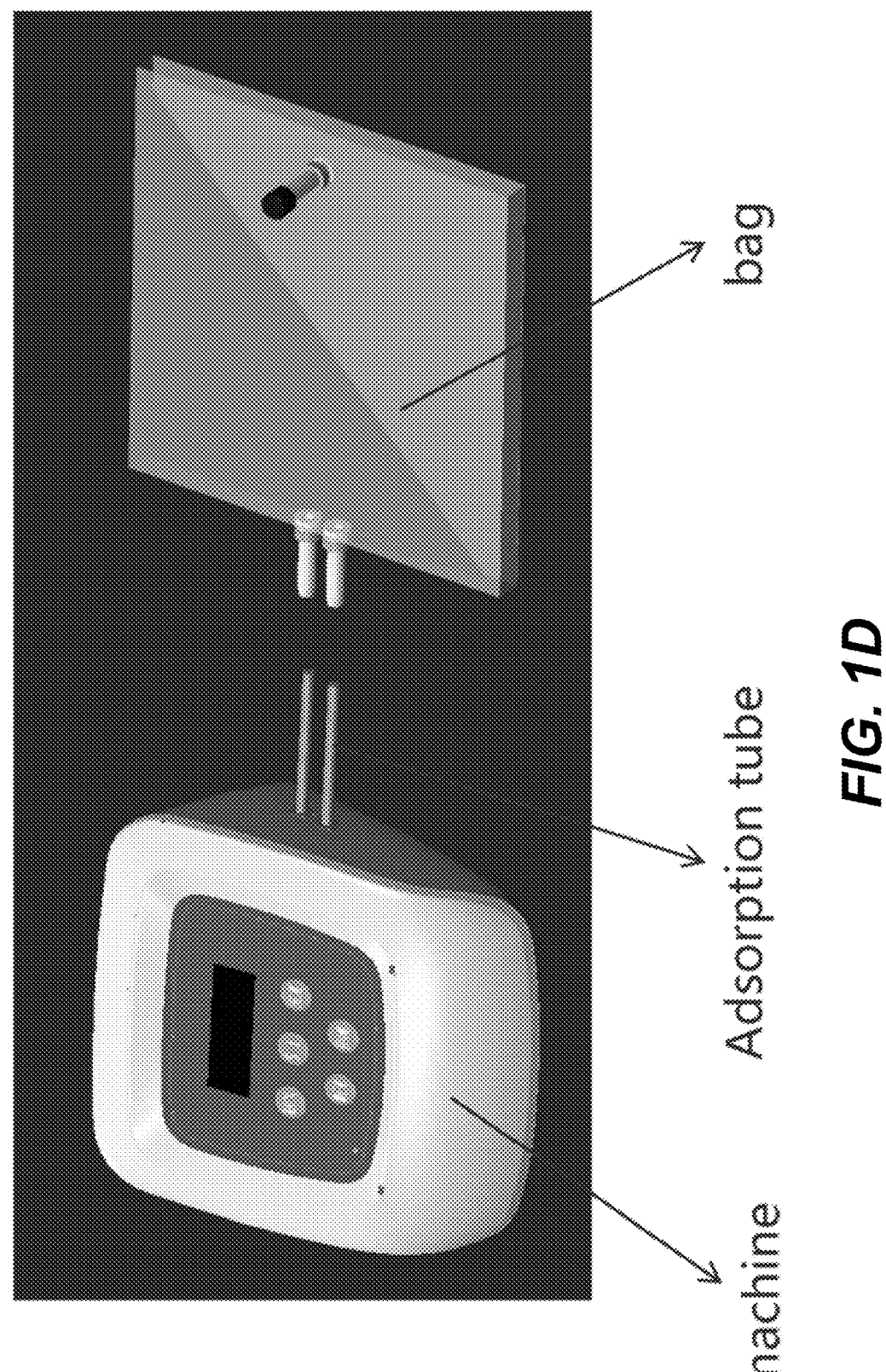
Figures 2A, 2B, 2C, 2D, 2E, 2F, 2G, 2H:
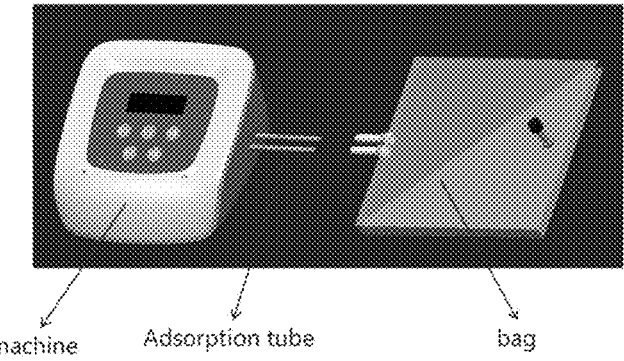
FIGS. 2A-2H show an exemplary compound capturing process using a compound capturing device disclosed herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include embodiments of a device for capturing one or more compounds in a gaseous sample. In some embodiments, the device comprises: one or more device inlets for attaching one or more gaseous sample capturing tubes. The device can comprise: a device outlet. The device can comprise: an electric pump connected to the one or more device inlets for drawing a gaseous sample, or a portion thereof, through the one or more device inlets and expelling the content of the gaseous sample, or a portion thereof, through the device outlet. The device can comprise: one or more sensors connected to the device inlets, the electric pump, and/or the device outlet via one or more air tubes. The device can include a display. The device can include: non-transitory memory configured to store executable instructions. The device can include: a microcontroller in communication with the electric pump, the one or more sensors, the display, and the non-transitory memory. The microcontroller can be programmed by the executable instructions to perform: causing the display to show a default gaseous sample capturing flow rate and a default gaseous sample collection duration. The microcontroller can be programmed by the executable instructions to perform: receiving a selected gaseous sample capturing flow rate and a selected gaseous sample capturing duration. The microcontroller can be programmed by the executable instructions to perform: causing the display to show a message to attach one or more gaseous sample capturing tubes to the one or more device inlets and a gaseous sample collection bag. The microcontroller can be programmed by the executable instructions to perform: receiving an input to proceed. The microcontroller can be programmed by the executable instructions to perform: causing the display to show a message requesting a gaseous sample to be collected through a bag inlet of the gaseous sample collection bag for a gaseous sample collection duration. The microcontroller can be programmed by the executable instructions to perform: showing on the display a countdown of the gaseous sample collection duration remaining. The microcontroller can be programmed by the executable instructions to perform: activating the electric pump to transfer the content in the gaseous sample collection bag, or a portion thereof, through the one or more gaseous sample capturing tubes, into the device via the one or more device inlets and out of the device via the device outlet, at the selected gaseous sample capturing flow rate for the selected gaseous sample capturing duration, thereby one or more compounds of the content in the gaseous sample collection bag, or a portion thereof, collected are captured onto the one or more gaseous sample capturing tubes.

Disclosed herein include embodiments of a system for capturing one or more compounds (e.g., volatile organic compounds (VOCs)) in a gaseous sample. In some embodiments, the system comprises: a device for capturing one or more compounds a gaseous sample of the present disclosure; and an external power source. The system can comprise: instructions for operating the device.

Disclosed herein include embodiments of a method for capturing VOCs. In some embodiments, the method comprises using a device for capturing one or more compounds of a gaseous sample of the present disclosure or a system for capturing one or more compounds of a gaseous sample of the present disclosure.

Disclosed herein include embodiments of a method for capturing VOCs. In some embodiments, the method comprises: displaying a default volatile organic compound (VOC) sample capturing flow rate and a default VOC capturing duration. The method can comprise: receiving a selected VOC capturing flow rate and a selected VOC capturing duration. The method can comprise: displaying a message to attach one or more VOC capturing tubes to one or more device inlets of a device for capturing VOC and a VOC collection bag. The method can comprise: receiving an input to proceed. The method can comprise: activating an electric pump of the device to transfer the content in the VOC collection bag through the one or more VOC capturing tubes, into the device via the one or more device inlets and out of the device via a device outlet, at the selected capturing flow rate for the selected capturing duration, thereby one or more VOCs in the content in the VOC collection bag are captured onto the one or more VOC capturing tubes.

Volatile Organic Compound Capturing

FIGS. 1A-1D show an exemplary compound (e.g., volatile organic compound (VOC)) capturing device and associated accessories, including exemplary sample capturing tubes and sample collection bag. The VOC capturing device can be compact and/or portable. The VOC capturing device can include a re-chargeable battery. The VOC capturing device for be used for capturing VOCs for the analysis and detecting physiological anomalies such as lung disease and certain types of gastrointestinal (GI) cancer. A VOC capturing system can include a VOC capturing device (see FIGS. 1A and 1D for examples), one or more VOC capturing tubes (see FIGS. 1B and 1D for examples), and one or more VOC sample collection bags (see FIGS. 1C and 1D for examples). VOC sample collection bag can be a disposable bag. A VOC capturing tube can be a reusable VOC capturing tube. A VOC capturing tube can be a disposable VOC capturing tube. A VOC capturing tube can be a single-use VOC capturing tube. FIG. 1A show an exemplary compound (e.g., volatile organic compound (VOC)) capturing device and associated accessories, including exemplary sample capturing tubes and sample collection bag.

FIGS. 2A-2H show an exemplary compound (e.g., VOC) capturing process using a compound (e.g., a VOC) capturing device. When the device is activated, the device can display an initial prompt for a duration, such as 1 second, 2 seconds, 3 seconds, 5 seconds, 10 seconds, or more (see FIG. 2A for an example). After the initial prompt, the device can ask a user (e.g., a subject, a patient, or an operator of the device) to detach any disposables and reusables (e.g., one or more sample capturing tubes and a VOC sample collection bag), if any, attached or connected to the device, from the device (see FIG. 2B for an example). A motor in the device can be activated to clear or purge any debris and/or VOC resides in the device (see FIG. 2C for an example). The device can generate a case number and display the case number to the user (see FIG. 2D for an example). The user can select a flow rate (e.g., between 50-200 ml/min) and a duration for VOC capturing (e.g., 60-300 seconds) (see FIG. 2E for an example). The device can ask the user to attach VOC capturing tubes (e.g., desorption tubes, such as thermal desorption tubes) and a VOC sample collection bag (see FIG. 2F for an example). The device can give a subject, which may or may not be the user, a VOC collection duration (e.g., 5 seconds, 10 seconds, 15 seconds, 20 seconds, 25 seconds, or more) to inflate the VOC sample collection bag to collect a VOC sample (see FIG. 2G for an example). The device can start collecting the VOC(s) in the VOC sample collection bag onto the VOC capturing tubes (see FIG. 2H for an example). The device can include sensors for determining the properties of the VOC sample after the VOC sample passes through the VOC capturing tubes, such as the temperature, the carbon dioxide ($CO_2$), and the relative humidity (RH) of the remaining VOC sample.

Compound Capturing

Figure 3A:
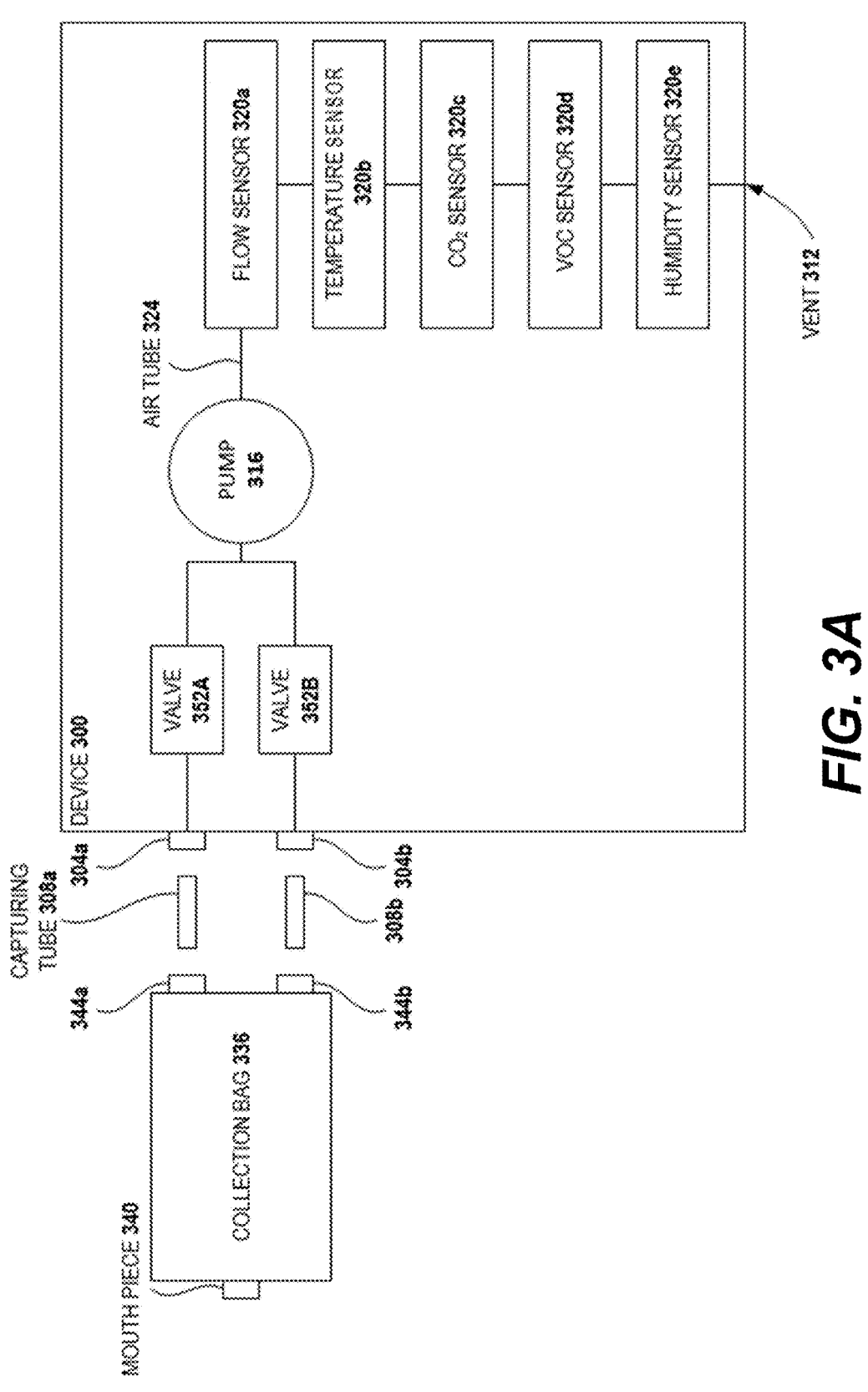
FIG. 3A shows a block diagram of exemplary pneumatic components of a compound capturing device.
Figure 3B:
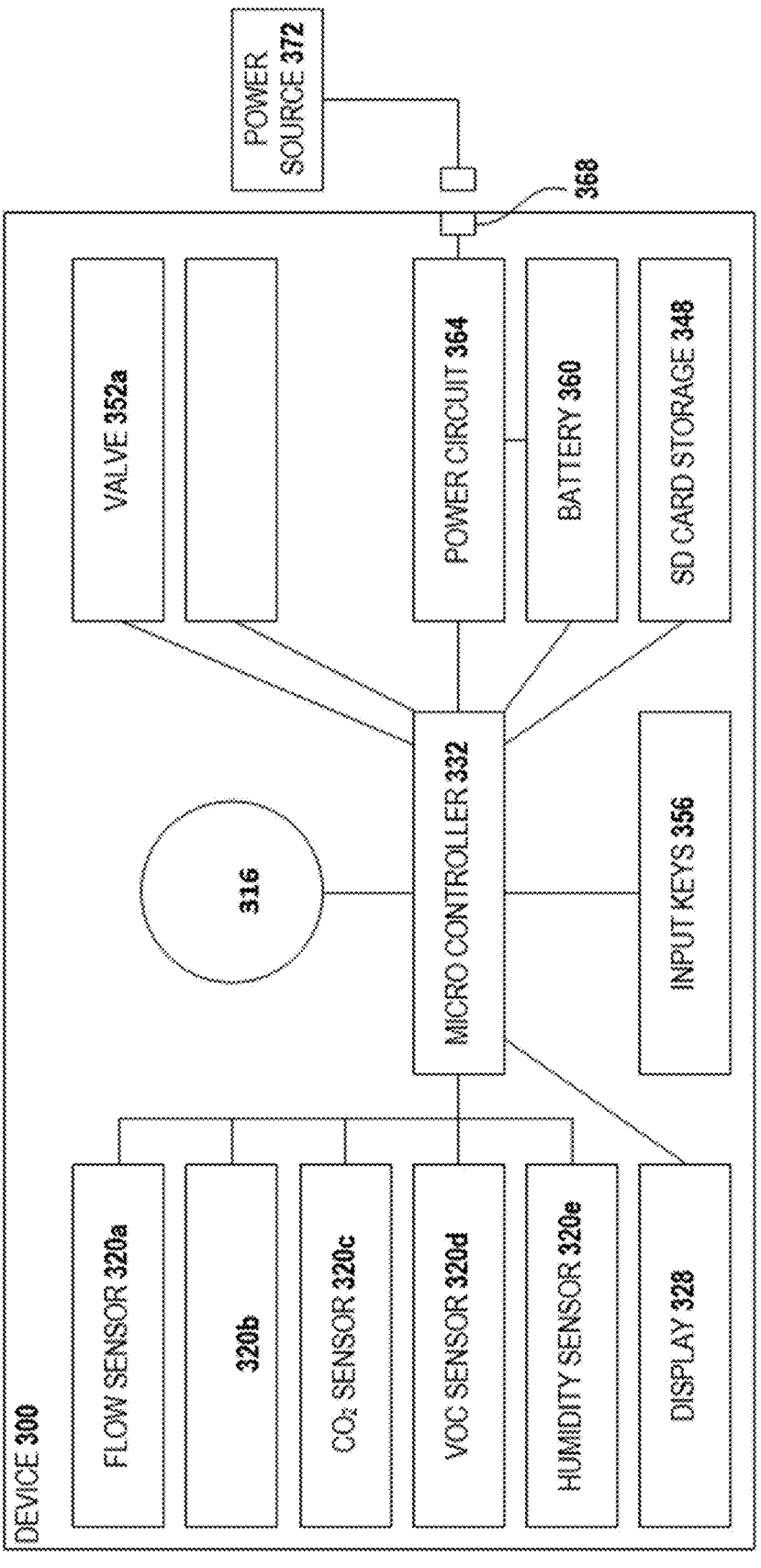
FIG. 3B shows a block diagram of exemplary electronic components of a compound capturing device.

FIG. 3A shows a block diagram of exemplary pneumatic components of a compound (e.g., VOC) capturing device 300. FIG. 3B shows a block diagram of exemplary electronic components of the compound capturing device 300. The device 300 can be used for capturing one or more compounds in a gaseous sample. The device 300 can comprise: one or more device inlets 304a, 304b for attaching gaseous sample capturing tubes 308a, 308b. The device 300 can comprise: a device outlet 312. The device 300 can comprise: an electric pump 316 connected to the one or more device inlets 304a, 304b for drawing (or intaking or sucking) a gaseous sample, or a portion thereof, through the one or more device inlets 304a, 304b and expelling (or displacing, blowing, or discharging) the content of the gaseous sample, or a portion thereof, through the device outlet 312. The device 300 can comprise: one or more sensors 320a-320e connected to the device inlets 304a, 304b, the electric pump 316, and/or the device outlet 312 via one or more air tubes 324 (e.g., elastic tubes).

In some embodiments, the device 300 can include a display 328. The device 300 can include: non-transitory memory configured to store executable instructions. The device 300 can include: a microcontroller 332 in communication with the electric pump 316, the one or more sensors 320a-320e, the display 328, and the non-transitory memory. The microcontroller 332 can be programmed by the executable instructions to perform: causing the display 328 to show a default gaseous sample capturing flow rate and a default gaseous sample collection duration. The microcontroller 332 can be programmed by the executable instructions to perform: receiving a selected gaseous sample capturing flow rate and a selected gaseous sample capturing duration. The microcontroller 332 can be programmed by the executable instructions to perform: using the default VOC capturing flow rate as the selected VOC capturing flow rate and/or the default VOC capturing duration as the selected VOC capturing duration if no selected gaseous sample capturing flow rate and/or selected gaseous sample capturing duration were received.

The microcontroller 332 can be programmed by the executable instructions to perform: causing the display 328 to show a message to attach one or more gaseous sample capturing tubes 308a, 308b to the one or more device inlets 304a, 304b and a gaseous sample collection bag 336. The microcontroller 332 can be programmed by the executable instructions to perform: receiving an input to proceed. The microcontroller 332 can be programmed by the executable instructions to perform: causing the display 328 to show a message requesting a gaseous sample to be collected through a bag inlet 340 (e.g., an air inlet pipe) of the gaseous sample collection bag 336 for a gaseous sample collection duration. The microcontroller 332 can be programmed by the executable instructions to perform: showing on the display 328 a countdown of the gaseous sample collection duration remaining. The microcontroller 332 can be programmed by the executable instructions to perform: activating the electric pump 316 to transfer the content in the gaseous sample collection bag 336, or a portion thereof, through the one or more gaseous sample capturing tubes 308a, 308b, into the device 300 via the one or more device inlets 304a, 304b and out of the device 3300 via the device outlet 312, at the selected gaseous sample capturing flow rate for the selected gaseous sample capturing duration, thereby one or more compounds (e.g., VOCs) of the content in the gaseous sample collection bag 336, or a portion thereof, collected are captured onto the one or more gaseous sample capturing tubes 308a, 308b. In some embodiments, the one or more device inlets 304a, 304b are identical. The one or more device inlets 304a, 304b can be adjacent (e.g., immediately adjacent) to each other.

Attaching

In some embodiments, causing the display 328 to show the message to attach the one or more gaseous sample capturing tubes 308a, 308b to the one or more device inlets 304a, 304b and the gaseous sample collection bag 336 comprises: causing the display 328 to show the message to attach a first tube opening of each of one or more gaseous sample capturing tubes 308a, 308b to a different device inlet of the one or more device inlets 304a, 304b and attach a second tube opening of each of the one or more gaseous sample capturing tubes 308a, 308b to a different bag outlet of one or more bag outlets 344a, 344b (e.g., air outlet pipes) of the gaseous sample collection bag 336.

Detaching

In some embodiments, the microcontroller 332 is programmed by the executable instructions to perform: causing the display 328 to show a message for any gaseous sample capturing tube attached to the one or more device inlets 304a, 304b to be detached from the one or more device inlets 304a, 304b. The microcontroller can be programmed by the executable instructions to perform: receiving an input to proceed. The microcontroller can be programmed by the executable instructions to perform: activating the electric pump 316 at a purging flow rate for a purging duration. The microcontroller 316 can be programmed by the executable instructions to perform: showing on the display 328 a countdown of the purging duration remaining.

After clearing or purging any debris and/or compound residues (e.g., VOC residues) from the prior use of the device 300 in the device 300, the air tubes 324 can be filled with air before the gaseous sample capturing tubes 308a, 308b (e.g., thermal desorption tubes) are connected. The purging process can ensure that compounds such as VODs not from the collection bag 336 do not enter into the gaseous sample capturing tubes 308a, 308b.

Sensors

In some embodiments, the one or more sensors comprises a flow rate sensor 320a, a temperature sensor 320b, a pressure sensor, a carbon dioxide ($CO_2$) sensor 320c, a volatile organic compound (VOC) sensor 320d, a humidity sensor 320e, or a combination thereof. A sensor connected to the electric pump 316 can comprise a flow rate sensor 320a. The flow sensor readings can be used to adjust the power output of the motor of the electric pump 316. In some embodiments, the power output of the motor of the electric pump 316 is determined (e.g., predetermined) based on the selected flow rate. For example, the power output of the motor of the electric pump 316 translates to the selected flow rate and is directly determined using the selected flow rate. In some embodiments, the power output of the motor of the electric pump 316 is adjusted based on the selected flow rate and the flow sensor readings measured by the flow rate sensor 320a. For example, an initial power output of the motor of the electric pump 316 can be determined based on the selected flow rate. The power output of the motor of the electric pump 316 can be adjusted based on the flow sensor reading(s). If the flow rate reading(s) measured by the flow rate sensor 320a are lower than the selected flow rate, the power output of the motor of the electric pump 316 can be increased (e.g., relative to the initial power output or the current power output) until the flow rate reading(s) measured by the flow rate sensor 320a are, or are comparable (e.g., within 1%, 2%, 3%, 4%, 5%, 6%, 7%, 8%, 9%, or 10%) to, the selected flow rate. If the flow rate reading(s) measured by the flow rate sensor 320a are higher than the selected flow rate, the power output of the motor of the electric pump 316 can be decreased (e.g., relative to the initial power output or the current power output) until the flow rate reading(s) measured by the flow rate sensor 320a are, or are to, the selected flow rate.

In some embodiments, sensor readings such as temperature sensor readings and $CO_2$ readings can be used to determine whether the gaseous sample is indeed a sample of interest (e.g., a human breath sample). The device 300 can show a message to the user of the device 300 that the gaseous sample appears to be a sample of interest or a warning message to the user of the device 300 that the gaseous sample does not appear to be a sample of interest.

In some embodiments, at least one of the one or more sensors 320a-320e is connected to the electric bump 316 and the device outlet 321 via at least one of the one or more air tubes 324. In some embodiments, at least one of the one or more sensors 320a-320e is connected to at least one of the one or more device inlets 304a, 304b and the electric bump 316 via at least one of the one or more air tubes 324.

In some embodiments, two or more sensors of the one or more sensors 320a-320e are connected sequentially as illustrated in FIG. 3A. In some embodiments, two or more sensors of the one or more sensors 320a-320e are connected in parallel.

In some embodiments, each sensor of the one or more sensors 320a-320e is connected to another sensor of the one or more sensors 320a-320e. For example, the flow sensor 320a is connected to the temperature sensor 320b in FIG. 3A. In some embodiments, each sensor of the one or more sensors 320a-320e other than a sensor connected to the electric pump (e.g., the flow rate sensor 320a shown in FIG. 3A) and a sensor connected to the device outlet (e.g., the humidity sensor 320e) is connected to two sensors of the one or more sensors. For example, the temperature sensor 320b, the $CO_2$ sensor 320c, and the VOC sensor 320d illustrated in FIG. 3A is each connected to two sensors.

Sample Information and Sensor Information

In some embodiments, the microcontroller is programmed by the executable instructions to perform: generating sample information. The microcontroller can be programmed by the executable instructions to perform: causing the display to show the sample information (e.g., a sample identification information, subject identification information, sample collection time, and date and time of the sample capturing). The sample identification information can be a sample identification number, such as a one-dimensional barcode or a two-dimensional barcode (e.g., a quick response (QR) code). The microcontroller can be programmed by the executable instructions to perform: receiving an input to proceed. In some embodiments, the microcontroller is programmed by the executable instructions to perform: causing the display to show a message requesting sample identification information. The microcontroller can be programmed by the executable instructions to perform: receiving the sample identification information.

In some embodiments, the microcontroller 332 is programmed by the executable instructions to perform, activating the electric pump 316 to transfer the content in the gaseous sample collection bag 336 through the one or more gaseous sample capturing tubes 304a, 304b, receiving sensor information from the one or more sensors 320a-320e. The microcontroller can be programmed by the executable instructions to perform: showing on the display 328 the sensor information, or a portion thereof. The microcontroller 332 can be programmed by the executable instructions to perform: generating a linkage relationship of the sensor information and sample information (e.g., a sample identification number, subject identification information, sample collection time, and date and time of the sample capturing) of the gaseous sample. The microcontroller 332 can be programmed by the executable instructions to perform: storing the sensor information, or a portion thereof, the sample information, any message shown to the user of the device (e.g., the sample appears, or does not appear, to be a sample of interest), and/or the linkage relationship in the non-transitory memory and/or a removable memory (e.g., a secure digital (SD) card storage 348). Alternatively or additionally, the microcontroller 332 can be programmed by the executable instructions to perform: transmitting the sensor information, or a portion thereof, the sample identification information, and/or the linkage relationship to a computing device, such as a remote computing device or a cloud computing device for storing sensor information, or a portion thereof, sample identification information, and/or linkage relationships of samples captured using the electronic pump device and/or other electronic pump devices.

Valves

In some embodiments, the device 300 comprises: one or more valves 352a, 352b (e.g., solenoid valves (SVs)) in communication with the microcontroller. Each of the one or more valves 352a, 352b in an opened state can allow the gaseous sample to enter into the device 300 via one or more of the one or more device inlets 304a, 304b the valve controls. Each of the one or more valves 352a, 352b in a closed state can prevent the gaseous sample from entering into the device 300 via one or more of the one or more device inlets 304a, 304b the valve controls. The one or more valves 352a, 352b can be in the closed state when the microcontroller is programmed by the executable instructions to perform: causing the display to show the message requesting the gaseous sample to be collected through the bag inlet 340 of the gaseous sample collection bag 336 for the gaseous sample collection duration. In some embodiments, the one or more valves 352a, 352b comprise one or more solenoid valves. Each of the one or more valves 352a, 352*b* can be connected to a different device inlet of the one or more device inlets 304*a*, 304*b*.

Device Input and Output

In some embodiments, the display 328 comprises a dot matrix display. In some embodiments, the display 328 comprises a touch screen display for receiving inputs (e.g., user inputs). In some embodiments, the device 300 comprising: one or more input keys 356 for receiving inputs. The one or more input keys 356 can comprise one or more membrane keys.

In some embodiments, the device 300 comprises: a battery 360 connected to the microcontroller 332 for powering the microcontroller 332 and the device 300. The device 300 can comprise: a power circuit 364 (e.g., a battery charging circuit) connected to the battery 360 for charging the battery 360. The power circuit 364 can be connected to the microcontroller 332 for powering the microcontroller 332 and the device 300. The device 300 can comprise: a power inlet 368 connected to the power circuit 364 for connecting the power circuit 364 to an external power source 372 (e.g., a 12V power supply).

Flow Rates

The default gaseous sample capturing flow rate (or any flow rate of the present disclosure) can be different in different embodiments. In some embodiments, the default gaseous sample capturing flow rate (or any flow rate of the present disclosure) is, or is about, 1 ml/min, 2 ml/min, 3 ml/min, 4 ml/min, 5 ml/min, 6 ml/min, 7 ml/min, 8 ml/min, 9 ml/min, 10 ml/min, 20 ml/min, 30 ml/min, 40 ml/min, 50 ml/min, 60 ml/min, 70 ml/min, 80 ml/min, 90 ml/min, 100 ml/min, 150 ml/min, 200 ml/min, 250 ml/min, 300 ml/min, 350 ml/min, 400 ml/min, 450 ml/min, 500 ml/min, 550 ml/min, 600 ml/min, 650 ml/min, 700 ml/min, 750 ml/min, 800 ml/min, 850 ml/min, 900 ml/min, 950 ml/min, 1000 ml/min, 1050 ml/min, 1100 ml/min, 1150 ml/min, 1200 ml/min, 1250 ml/min, 1300 ml/min, 1350 ml/min, 1400 ml/min, 1450 ml/min, 1500 ml/min, 1550 ml/min, 1600 ml/min, 1650 ml/min, 1700 ml/min, 1750 ml/min, 1800 ml/min, 1850 ml/min, 1900 ml/min, 1950 ml/min, 2000 ml/min, or a number or a range between any two of these values. In some embodiments, the default gaseous sample capturing flow rate (or any flow rate of the present disclosure) is at least, is at least about, is at most, or is at most about, 1 ml/min, 2 ml/min, 3 ml/min, 4 ml/min, 5 ml/min, 6 ml/min, 7 ml/min, 8 ml/min, 9 ml/min, 10 ml/min, 20 ml/min, 30 ml/min, 40 ml/min, 50 ml/min, 60 ml/min, 70 ml/min, 80 ml/min, 90 ml/min, 100 ml/min, 150 ml/min, 200 ml/min, 250 ml/min, 300 ml/min, 350 ml/min, 400 ml/min, 450 ml/min, 500 ml/min, 550 ml/min, 600 ml/min, 650 ml/min, 700 ml/min, 750 ml/min, 800 ml/min, 850 ml/min, 900 ml/min, 950 ml/min, 1000 ml/min, 1050 ml/min, 1100 ml/min, 1150 ml/min, 1200 ml/min, 1250 ml/min, 1300 ml/min, 1350 ml/min, 1400 ml/min, 1450 ml/min, 1500 ml/min, 1550 ml/min, 1600 ml/min, 1650 ml/min, 1700 ml/min, 1750 ml/min, 1800 ml/min, 1850 ml/min, 1900 ml/min, 1950 ml/min, or 2000 ml/min. For example, default gaseous sample capturing flow rate can be about 50 ml/minute to about 200 ml/min.

The selected gaseous sample capturing flow rate (or any flow rate of the present disclosure) can be different in different embodiments. In some embodiments, the selected gaseous sample capturing flow rate (or any flow rate of the present disclosure) is, or is about, 1 ml/min, 2 ml/min, 3 ml/min, 4 ml/min, 5 ml/min, 6 ml/min, 7 ml/min, 8 ml/min, 9 ml/min, 10 ml/min, 20 ml/min, 30 ml/min, 40 ml/min, 50 ml/min, 60 ml/min, 70 ml/min, 80 ml/min, 90 ml/min, 100 ml/min, 150 ml/min, 200 ml/min, 250 ml/min, 300 ml/min, 350 ml/min, 400 ml/min, 450 ml/min, 500 ml/min, 550 ml/min, 600 ml/min, 650 ml/min, 700 ml/min, 750 ml/min, 800 ml/min, 850 ml/min, 900 ml/min, 950 ml/min, 1000 ml/min, 1050 ml/min, 1100 ml/min, 1150 ml/min, 1200 ml/min, 1250 ml/min, 1300 ml/min, 1350 ml/min, 1400 ml/min, 1450 ml/min, 1500 ml/min, 1550 ml/min, 1600 ml/min, 1650 ml/min, 1700 ml/min, 1750 ml/min, 1800 ml/min, 1850 ml/min, 1900 ml/min, 1950 ml/min, 2000 ml/min, or a number or a range between any two of these values. In some embodiments, the selected gaseous sample capturing flow rate (or any flow rate of the present disclosure) is at least, is at least about, is at most, or is at most about, 1 ml/min, 2 ml/min, 3 ml/min, 4 ml/min, 5 ml/min, 6 ml/min, 7 ml/min, 8 ml/min, 9 ml/min, 10 ml/min, 20 ml/min, 30 ml/min, 40 ml/min, 50 ml/min, 60 ml/min, 70 ml/min, 80 ml/min, 90 ml/min, 100 ml/min, 150 ml/min, 200 ml/min, 250 ml/min, 300 ml/min, 350 ml/min, 400 ml/min, 450 ml/min, 500 ml/min, 550 ml/min, 600 ml/min, 650 ml/min, 700 ml/min, 750 ml/min, 800 ml/min, 850 ml/min, 900 ml/min, 950 ml/min, 1000 ml/min, 1050 ml/min, 1100 ml/min, 1150 ml/min, 1200 ml/min, 1250 ml/min, 1300 ml/min, 1350 ml/min, 1400 ml/min, 1450 ml/min, 1500 ml/min, 1550 ml/min, 1600 ml/min, 1650 ml/min, 1700 ml/min, 1750 ml/min, 1800 ml/min, 1850 ml/min, 1900 ml/min, 1950 ml/min, or 2000 ml/min. For example, the selected gaseous sample capturing flow rate can be about 50 ml/minute to about 200 ml/min.

The purging flow rate (or any flow rate of the present disclosure) can be different in different embodiments. In some embodiments, the purging flow rate (or any flow rate of the present disclosure) is, or is about, 1 ml/min, 2 ml/min, 3 ml/min, 4 ml/min, 5 ml/min, 6 ml/min, 7 ml/min, 8 ml/min, 9 ml/min, 10 ml/min, 20 ml/min, 30 ml/min, 40 ml/min, 50 ml/min, 60 ml/min, 70 ml/min, 80 ml/min, 90 ml/min, 100 ml/min, 150 ml/min, 200 ml/min, 250 ml/min, 300 ml/min, 350 ml/min, 400 ml/min, 450 ml/min, 500 ml/min, 550 ml/min, 600 ml/min, 650 ml/min, 700 ml/min, 750 ml/min, 800 ml/min, 850 ml/min, 900 ml/min, 950 ml/min, 1000 ml/min, 1050 ml/min, 1100 ml/min, 1150 ml/min, 1200 ml/min, 1250 ml/min, 1300 ml/min, 1350 ml/min, 1400 ml/min, 1450 ml/min, 1500 ml/min, 1550 ml/min, 1600 ml/min, 1650 ml/min, 1700 ml/min, 1750 ml/min, 1800 ml/min, 1850 ml/min, 1900 ml/min, 1950 ml/min, 2000 ml/min, or a number or a range between any two of these values. In some embodiments, the purging capturing flow rate (or any flow rate of the present disclosure) is at least, is at least about, is at most, or is at most about, 1 ml/min, 2 ml/min, 3 ml/min, 4 ml/min, 5 ml/min, 6 ml/min, 7 ml/min, 8 ml/min, 9 ml/min, 10 ml/min, 20 ml/min, 30 ml/min, 40 ml/min, 50 ml/min, 60 ml/min, 70 ml/min, 80 ml/min, 90 ml/min, 100 ml/min, 150 ml/min, 200 ml/min, 250 ml/min, 300 ml/min, 350 ml/min, 400 ml/min, 450 ml/min, 500 ml/min, 550 ml/min, 600 ml/min, 650 ml/min, 700 ml/min, 750 ml/min, 800 ml/min, 850 ml/min, 900 ml/min, 950 ml/min, 1000 ml/min, 1050 ml/min, 1100 ml/min, 1150 ml/min, 1200 ml/min, 1250 ml/min, 1300 ml/min, 1350 ml/min, 1400 ml/min, 1450 ml/min, 150 ml/min, 1550 ml/min, 1600 ml/min, 1650 ml/min, 1700 ml/min, 1750 ml/min, 1800 ml/min, 1850 ml/min, 1900 ml/min, 1950 ml/min, or 2000 ml/min. For example, the purging flow rate can be about 50 ml/minute to about 200 ml/minute.

Duration

The default gaseous sample capturing duration (or any duration of the present disclosure) can be different in different embodiments. In some embodiments, the default gaseous sample capturing duration (or any duration of the present disclosure) is, or is about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, or a number or a range between any two of these values. In some embodiments, the default gaseous sample capturing duration (or any duration of the present disclosure) is at least, is at least about, is at most, or is at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, or 60 mins. For example, the default gaseous sample capturing duration can be about 1 minute to about 5 minutes.

The selected gaseous sample capturing duration (or any duration of the present disclosure) can be different in different embodiments. In some embodiments, the selected gaseous sample capturing duration (or any duration of the present disclosure) is, or is about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, or a number or a range between any two of these values. In some embodiments, the selected gaseous sample capturing duration (or any duration of the present disclosure) is at least, is at least about, is at most, or is at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, or 60 mins. For example, the selected gaseous sample capturing duration can be about 1 minute to about 5 minutes.

The purging duration (or any duration of the present disclosure) can be different in different embodiments. In some embodiments, the purging duration (or any duration of the present disclosure) is, or is about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins, or a number or a range between any two of these values. In some embodiments, the purging duration (or any duration of the present disclosure) is at least, is at least about, is at most, or is at most about, 1 sec, 2 secs, 3 secs, 4 secs, 5 secs, 6 secs, 7 secs, 8 secs, 9 secs, 10 secs, 11 secs, 12 secs, 13 secs, 14 secs, 15 secs, 16 secs, 17 secs, 18 secs, 19 secs, 20 secs, 21 secs, 22 secs, 23 secs, 24 secs, 25 secs, 26 secs, 27 secs, 28 secs, 29 secs, 30 secs, 31 secs, 32 secs, 33 secs, 34 secs, 35 secs, 36 secs, 37 secs, 38 secs, 39 secs, 40 secs, 41 secs, 42 secs, 43 secs, 44 secs, 45 secs, 46 secs, 47 secs, 48 secs, 49 secs, 50 secs, 51 secs, 52 secs, 53 secs, 54 secs, 55 secs, 56 secs, 57 secs, 58 secs, 59 secs, 1 min, 2 mins, 3 mins, 4 mins, 5 mins, 6 mins, 7 mins, 8 mins, 9 mins, 10 mins, 11 mins, 12 mins, 13 mins, 14 mins, 15 mins, 16 mins, 17 mins, 18 mins, 19 mins, 20 mins, 21 mins, 22 mins, 23 mins, 24 mins, 25 mins, 26 mins, 27 mins, 28 mins, 29 mins, 30 mins, 31 mins, 32 mins, 33 mins, 34 mins, 35 mins, 36 mins, 37 mins, 38 mins, 39 mins, 40 mins, 41 mins, 42 mins, 43 mins, 44 mins, 45 mins, 46 mins, 47 mins, 48 mins, 49 mins, 50 mins, 51 mins, 52 mins, 53 mins, 54 mins, 55 mins, 56 mins, 57 mins, 58 mins, 59 mins, 60 mins. For example, the purging duration can be about 10 seconds to 60 seconds.

In some embodiments, the gaseous sample collection duration is about 5 seconds to 20 seconds.

Collected and Captured Sample Volumes

The expected volume of the gaseous sample (e.g., the subject's breath or the patient's breath) collected in the gaseous sample collection bag during the gaseous sample collection duration can be different in different embodiments. In some embodiments, the expected volume of the gaseous sample collected in the gaseous sample collection bag during the gaseous sample collection duration (or any volume of the present disclosure) is, or is about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. In some embodiments, the expected volume of the gaseous sample collected in the gaseous sample collection bag during the gaseous sample collection duration (or any volume of the present disclosure) is at least, is at least about, is at most, or is at most about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. For example, the volume of breath of the subject collected in the gaseous sample collection bag during the gaseous sample collection duration can be expected to be about 2.5 liters.

The volume of the gaseous sample (e.g., the subject's breath or the patient's breath) collected in the gaseous sample collection bag during the gaseous sample collection duration can be different in different embodiments. In some embodiments, the volume of the gaseous sample collected in the gaseous sample collection bag during the gaseous sample collection duration (or any volume of the present disclosure) is, or is about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. In some embodiments, the volume of the gaseous sample collected in the gaseous sample collection bag during the gaseous sample collection duration (or any volume of the present disclosure) is at least, is at least about, is at most, or is at most about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. For example, the volume of breath of the subject collected in the gaseous sample collection bag during the gaseous sample collection duration can be about 2.5 liters.

The volume of the gaseous sample collected in the gaseous sample collection bag during the gaseous sample collection duration (e.g., the subject's breath or the patient's breath) that passes through the one or more gaseous sample capturing tubes can be different in different embodiments. In some embodiments, the volume of the gaseous sample capturing in the gaseous sample collection bag that passes through the one or more gaseous sample capturing tubes (or any volume of the present disclosure) is, or is about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. In some embodiments, the volume of the gaseous sample collected in the gaseous sample collection bag that passes through the one or more gaseous sample capturing tubes (or any volume of the present disclosure) is at least, is at least about, is at most, or is at most about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. For example, the volume of the gaseous sample collected in the gaseous sample collection bag that passes through the one or more gaseous sample capturing tubes can be about 2 liters.

Air Tubes

In some embodiments, one or each of the one or more air tubes 324 is rigid, semi-rigid, and/or elastic. One or each of the one or more air tubes 324 can comprise a low durometer low pressure tubing that can stretch. Non-limiting exemplary examples of a material of one or each of the one of the air tubes 324 include latex, rubber, silicone, or a combination thereof.

In some embodiments, the electric pump 316 is a diaphragm pump. A diaphragm pump can generate air flow that is not perfectly smooth but has ripples. The right size motor can be selected to limit the ripple for the targeted flow rate. Because the device 300 can handle a wide range of flow rates, such as 50-200 ml/min, the electric pump 316 can include an elastic tube attached after the electric pump 316 and before the first sensor (e.g., a flow rate sensor 320a). When the electric pump 316 is activated, air coming into the elastic tube can have some ripples but the air going out of the elastic tube can be constant (or more constant).

Sample Collection Bag

Figure 4A:
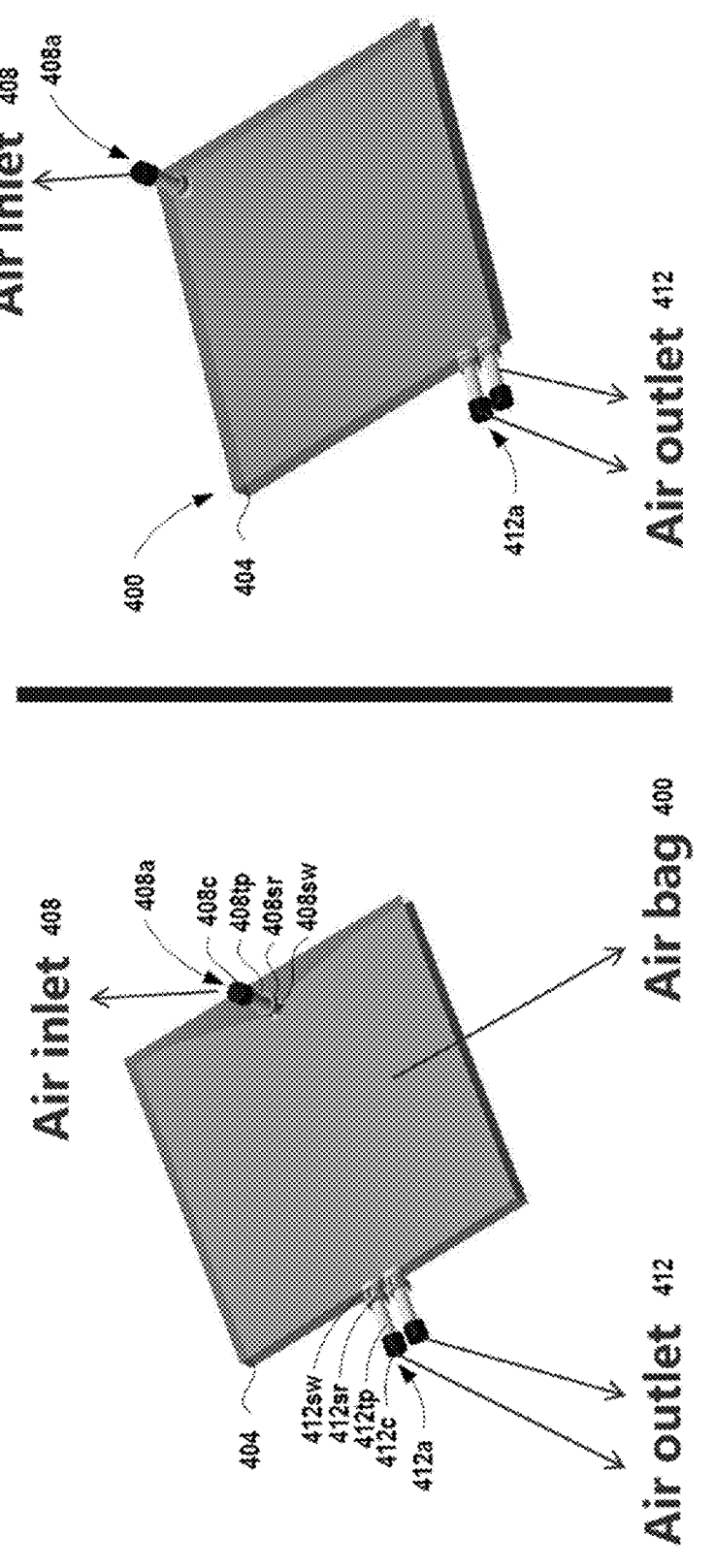
FIGS. 4A-4D show exemplary sample collection bags.
Figure 4A:
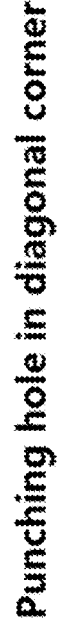
Figure 4B:
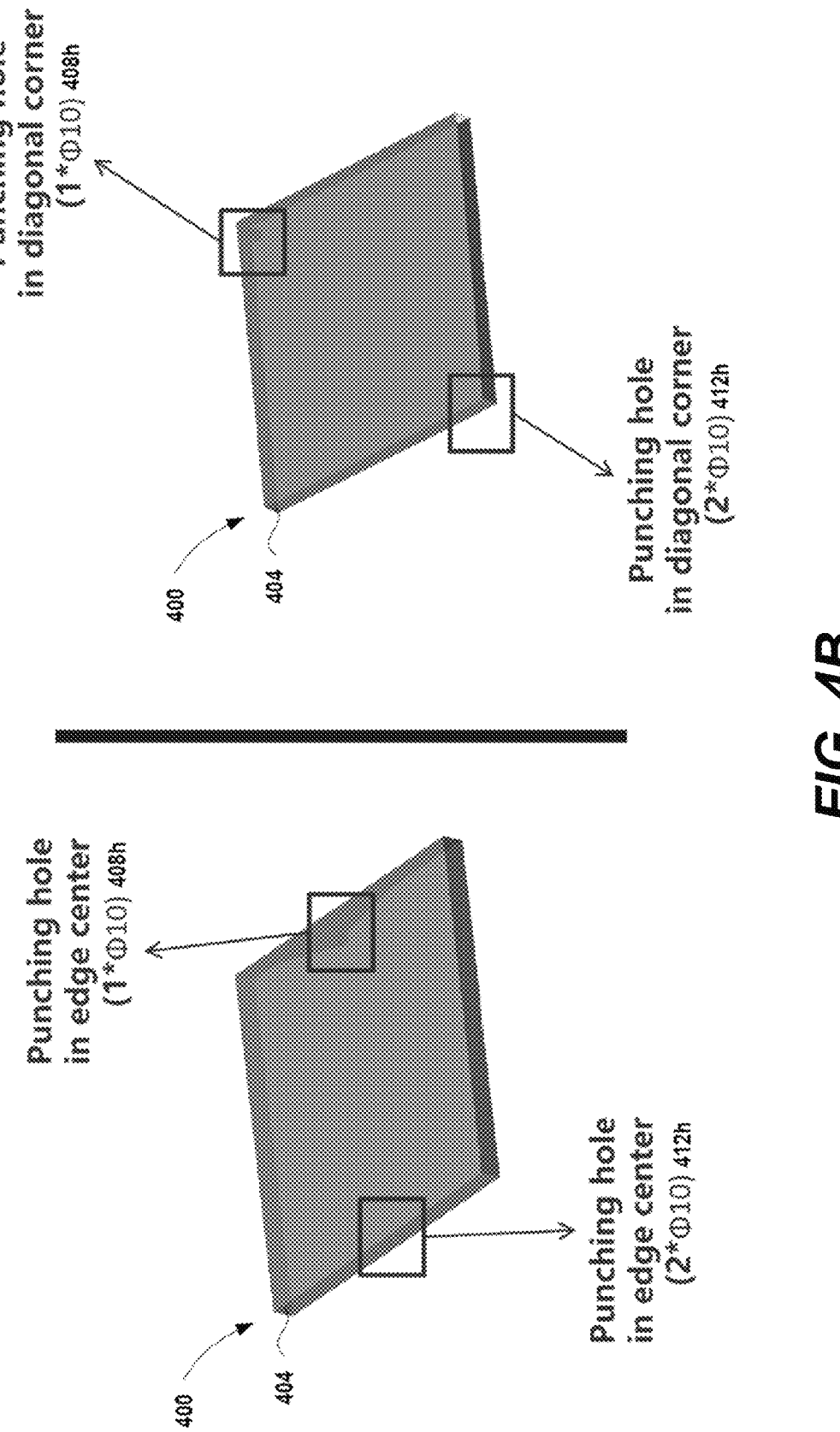
Figure 4C:
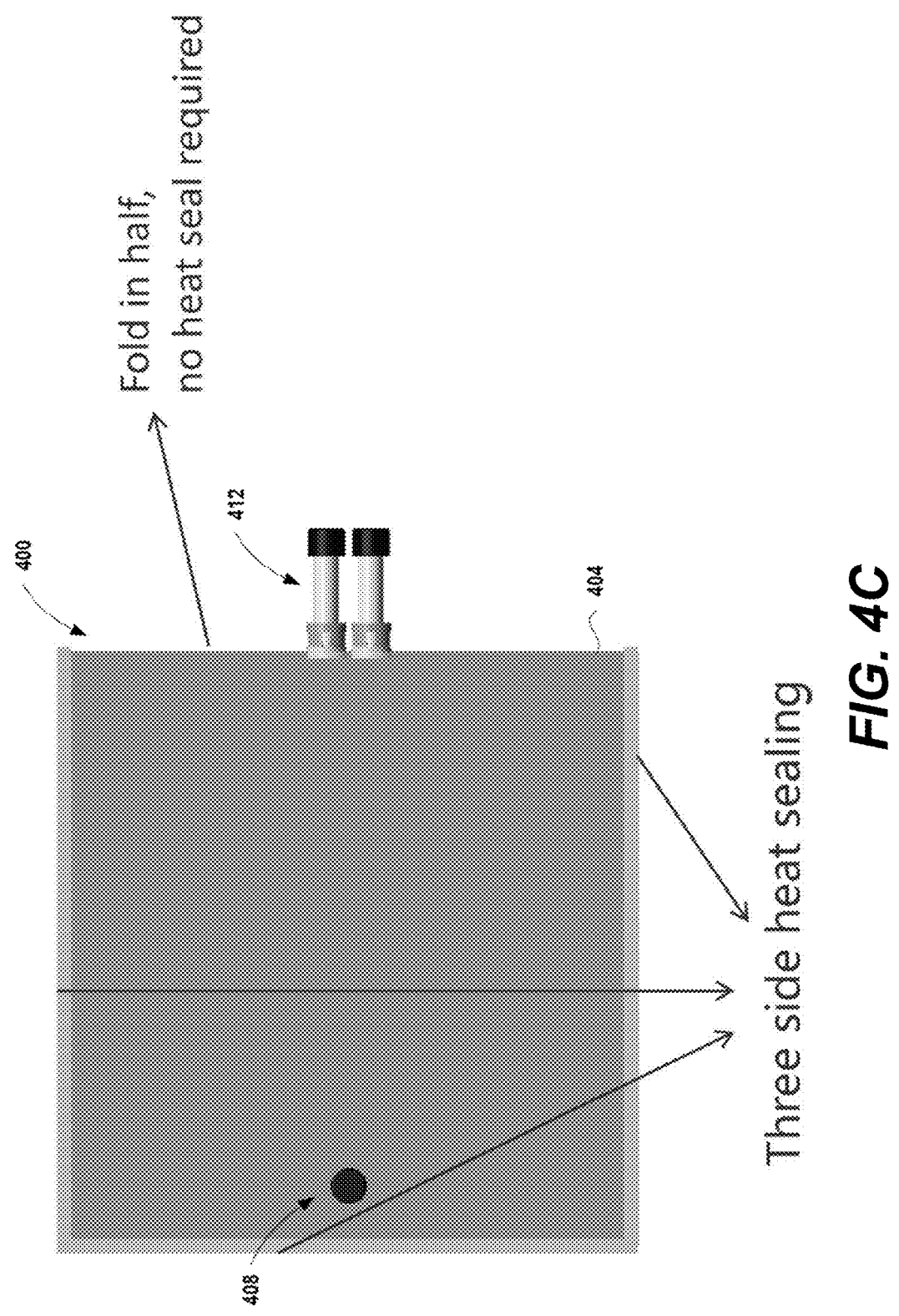
Figure 4D:
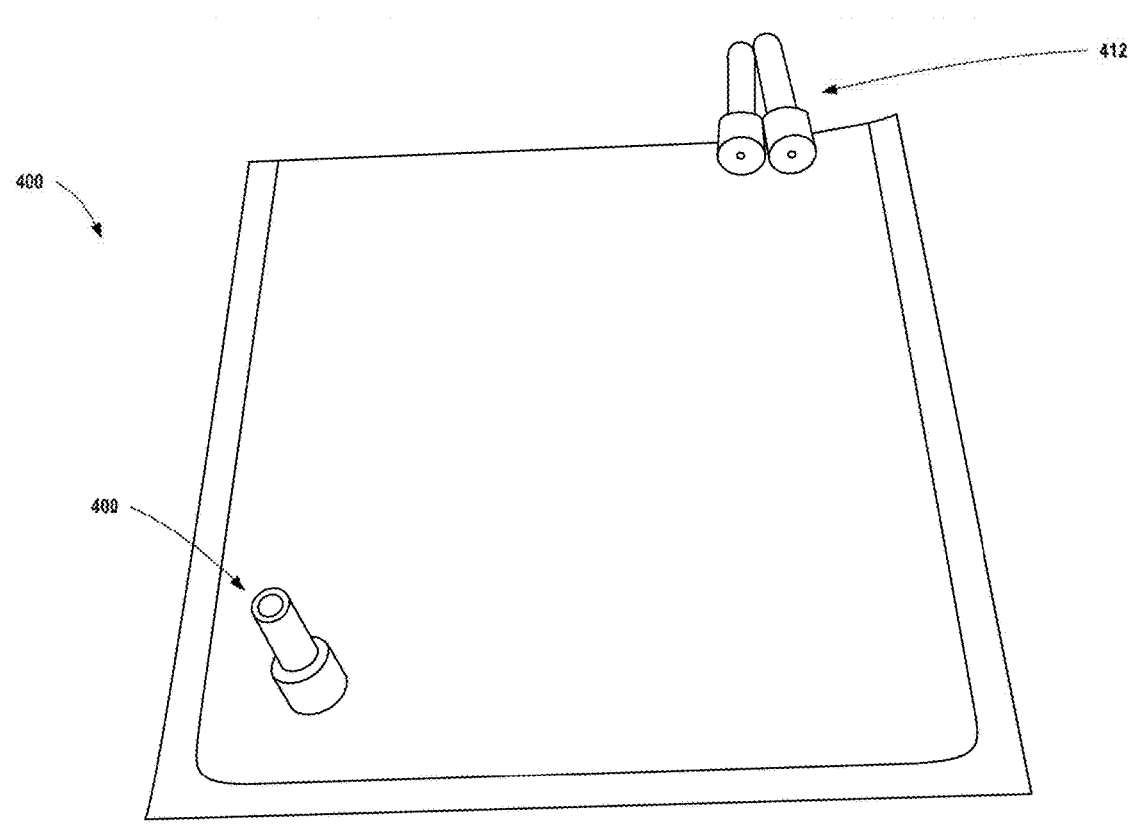

FIGS. 4A-4D show exemplary sample collection bags. FIG. 4A shows example sample collection bags. FIG. 4B shows exemplary sample collection bag hole positions. FIGS. 4C and 4D shows exemplary sample collection bag sealing (e.g., heat sealing). A gaseous sample collection bag 400 (e.g., a VOC collection bag) can comprise a bag body 404. The bag body 404 can be sealed (e.g., heat sealed) on one or more sides, on two or more sides, on three or more sides, on three sides (See FIGS. 4C and 4D for illustrations), and on four sides. The bag body 404 can be sealed (e.g., heat sealed) on all sides except one side. The bag body can comprise a sheet (e.g., a plastic sheet) folded and sealed (e.g., heat sealed) on all sides except the folded side. The bag body 404 can be rectangular or square in shape when prior to use or when deflated. The bag body 404 can be transparent or opaque. A material of the bag body 404 can comprise high-density polyethylene (HDPE), low-density polyethylene (LDPE), and/or linear low-density polyethylene (LL-DPE). A material of the bag body and/or a sealed side of the bag body can be impermeable to air. A material of the bag body and/or a sealed side of the bag body can be impermeable to one or more volatile organic compounds.

A bag inlet 408 can comprise an inlet assembly 408*a* comprising a threaded inlet pipe 408*tp*, an inlet sealing washer 408*sw*, and an inlet snap ring 408*sr*. The threaded inlet pipe 408*tp* can be attached to an inlet hole 408*h* of the gaseous sample collection bag 400 by the inlet sealing washer 408*sw* and the inlet snap ring 408*sr*. The inlet hole 408*h* can be on an edge or adjacent to an edge of the gaseous sample collection bag 400 (See FIGS. 4A-4B left panels for illustrations). The inlet hole 408*h* can be on a diagonal or adjacent to a diagonal of the gaseous sample collection bag 400 (See FIGS. 4A-4B right panels for illustrations). The inlet assembly 408*a* can comprise an inlet cap 408*c* for preventing the gaseous sample to enter or exit the gaseous sample collection bag in some configurations (e.g., before sample collection, and during sample capturing).

Each of the bag outlets 412 can comprise an outlet assembly 412*a* comprising a threaded outlet pipe 412*tp*, an outlet sealing washer 412*sw*, and an outlet snap ring 412*sr*. The threaded outlet pipe 412*tp* can be attached to an outlet hole 412*h* of the gaseous sample collection bag 400*a* by the outlet sealing washer 412*sw* and the outlet snap ring 412*sr*. The outlet hole 412*h* can be on an edge or adjacent to an edge of the gaseous bag body 404 (See FIGS. 4A-4B left panels for illustrations). The outlet hole 408*h* can be on a diagonal or adjacent to a diagonal of the bag body 404 (See FIGS. 4A-4B right panels for illustrations). The outlet assembly 412*a* can comprise an outlet cap 412*c* for preventing the gaseous sample to enter or exit the gaseous sample collection bag in some configurations (e.g., before sample collection, before being inflated, or when deflated). In some embodiments, the one or more bag outlets 412 are identical. The one or more bag outlets 412 can be adjacent to each other.

The one or more bag outlets 412 and the bag inlet 408 can be identical. One, or each, of the one or more bag outlets 412 (or the bag outlet assemblies 408*a*) can be perpendicular or approximately perpendicular (e.g., within 1°, 2°, 3°, 4°, 5°, 6°, 7°, 8°, 9°, or) 10° to the bag inlet 408 (or the bag inlet assembly 408*a*). The one or more bag outlets 412 (or the bag outlet assembly 408*a*) and the bag inlet 408 (or the bag inlet assembly 408*a*) can be on different surfaces of the bag body 404. The one or more bag outlets 412 (or the bag outlet assembly 408*a*) and the bag inlet 408 (or the bag inlet assembly 408*a*) can be on an identical surface of the bag body 404.

The dimensionality of a sample collection bag can be different in different embodiments. In some embodiments, a dimension (e.g., the width, the depth, the height, the radius, the diameter, or the circumference) of a sample collection bag is, or is about, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 60 cm, 70 cm, 80 cm, 90 cm, 100 cm, or a number or a range between any two of these values. In some embodiments, a dimension (e.g., the width, the depth, the height, the radius, the diameter, or the circumference) of a sample collection bag is at least, is at least about, is at most, or is at most about, 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, 50 cm, 60 cm, 70 cm, 80 cm, 90 cm, or 100 cm. In some embodiments, a dimension (e.g., the width, the depth, the height, the radius, the diameter, or the circumference) of a sample collection bag is, or is about, 1 in, 2 in, 3 in, 4 in, 5 in, 6 in, 7 in, 8 in, 9 in, 10 in, 11 in, 12 in, 13 in, 14 in, 15 in, 16 in, 17 in, 18 in, 19 in, 20 in, 21 in, 22 in, 23 in, 24 in, 25 in, 26 in, 27 in, 28 in, 29 in, 30 in, 31 in, 32 in, 33 in, 34 in, 35 in, 36 in, 37 in, 38 in, 39 in, 40 in, 41 in, 42 in, 43 in, 44 in, 45 in, 46 in, 47 in, 48 in, 49 in, 50 in, or a number of a range between any two of these values. In some embodiments, a dimension (e.g., the width, the depth, the height, the radius, the diameter, or the circumference) of a sample collection bag is at least, is at least about, is at most, or is at most about, 1 in, 2 in, 3 in, 4 in, 5 in, 6 in, 7 in, 8 in, 9 in, 10 in, 11 in, 12 in, 13 in, 14 in, 15 in, 16 in, 17 in, 18 in, 19 in, 20 in, 21 in, 22 in, 23 in, 24 in, 25 in, 26 in, 27 in, 28 in, 29 in, 30 in, 31 in, 32 in, 33 in, 34 in, 35 in, 36 in, 37 in, 38 in, 39 in, 40 in, 41 in, 42 in, 43 in, 44 in, 45 in, 46 in, 47 in, 48 in, 49 in, or 50 in. For example, the sample collection bag can have a width of 25 cm and a depth of 24 cm.

The volume of the gaseous sample collection bag can be different in different embodiments. In some embodiments, the volume of the gaseous sample collection bag (or any volume of the present disclosure) is, or is about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. In some embodiments, the volume of the gaseous sample collection bag (or any volume of the present disclosure) is at least, is at least about, is at most, or is at most about, 0.5 liter, 0.6 liters, 0.7 liters, 0.8 liters, 0.9 liters, 1 liter, 1.1 liters, 1.2 liters, 1.3 liters, 1.4 liters, 1.5 liters, 1.6 liters, 1.7 liters, 1.8 liters, 1.9 liters, 2 liters, 2.1 liters, 2.2 liters, 2.3 liters, 2.4 liters, 2.5 liters, 2.6 liters, 2.7 liters, 2.8 liters, 2.9 liters, 3 liters, 3.1 liters, 3.2 liters, 3.3 liters, 3.4 liters, 3.5 liters, 3.6 liters, 3.7 liters, 3.8 liters, 3.9 liters, 4 liters, 4.1 liters, 4.2 liters, 4.3 liters, 4.4 liters, 4.5 liters, 4.6 liters, 4.7 liters, 4.8 liters, 4.9 liters, 5 liters, or a number or a range between any two of these values. For example, the volume of the VOC collection bag during the gaseous sample collection duration can be about 2.5 liters.

The inlet hole, or the outlet hole, can be round or oval in shape. A dimension (e.g., the radius, the diameter, or the circumference) of the inlet hole, or the outlet hole, can be different in different embodiments. In some embodiments, a dimension of the inlet hole, or the outlet hole, is, or is about, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, or a number or a range between any of these values. In some embodiments, a dimension of the inlet hole, or the outlet hole, is at least, is at least about, is at most, or is at most about, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, a dimension of the inlet hole, or the outlet hole, is, or is about, 0.1 in, 0.2 in, 0.3 in, 0.4 in, 0.5 in, 0.6 in, 0.7 in, 0.8 in, 0.9 in, 1 in, or a number or a range between any of these values. In some embodiments, a dimension of the inlet hole, or the outlet hole, is at least, is at least about, is at most, or is at most about, 0.1 in, 0.2 in, 0.3 in, 0.4 in, 0.5 in, 0.6 in, 0.7 in, 0.8 in, 0.9 in, or 1 in.

Figure 5A:
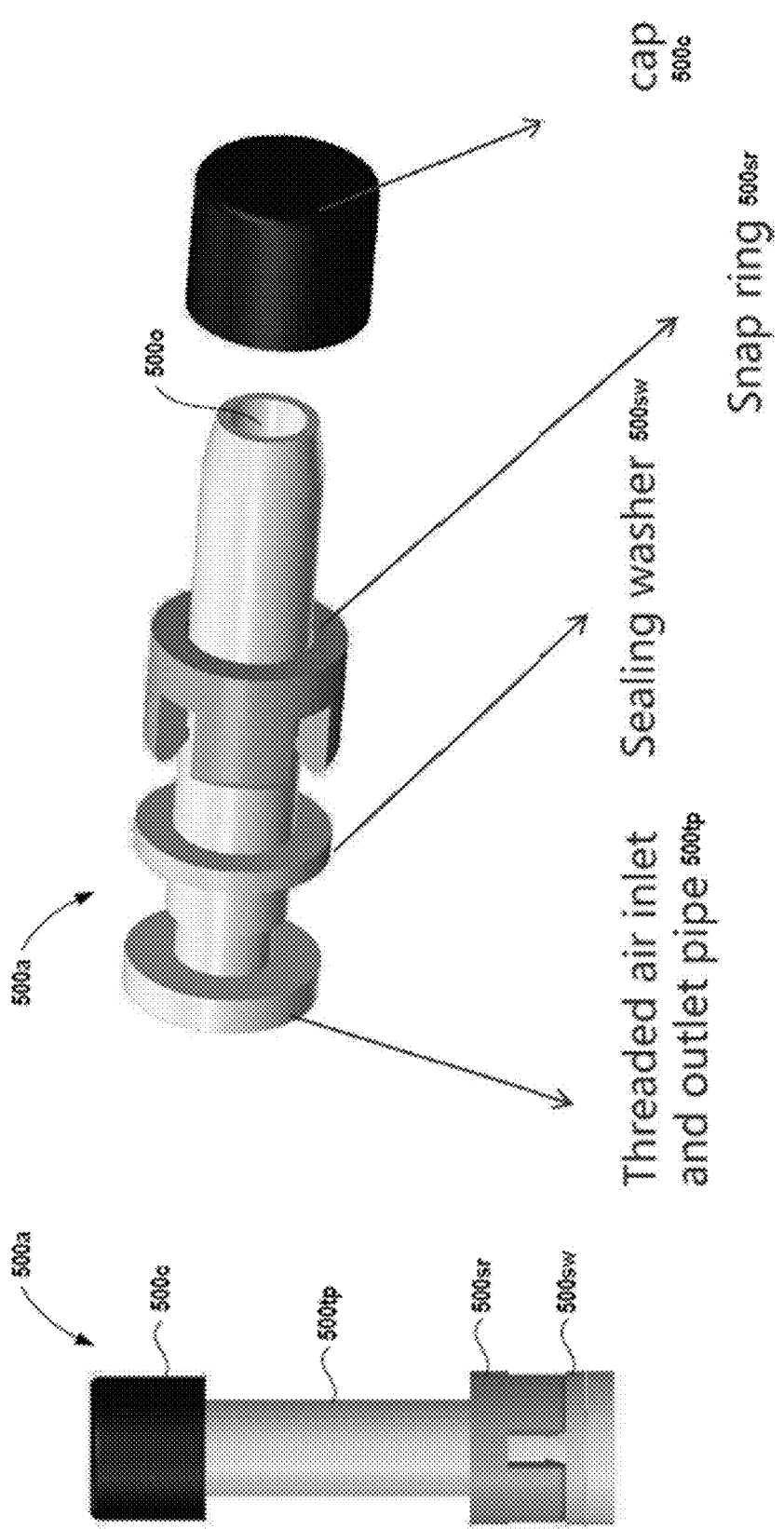
FIGS. 5A-5B show an exemplary inlet and outlet pipe assembly of a sample collection bag.
Figure 5B:
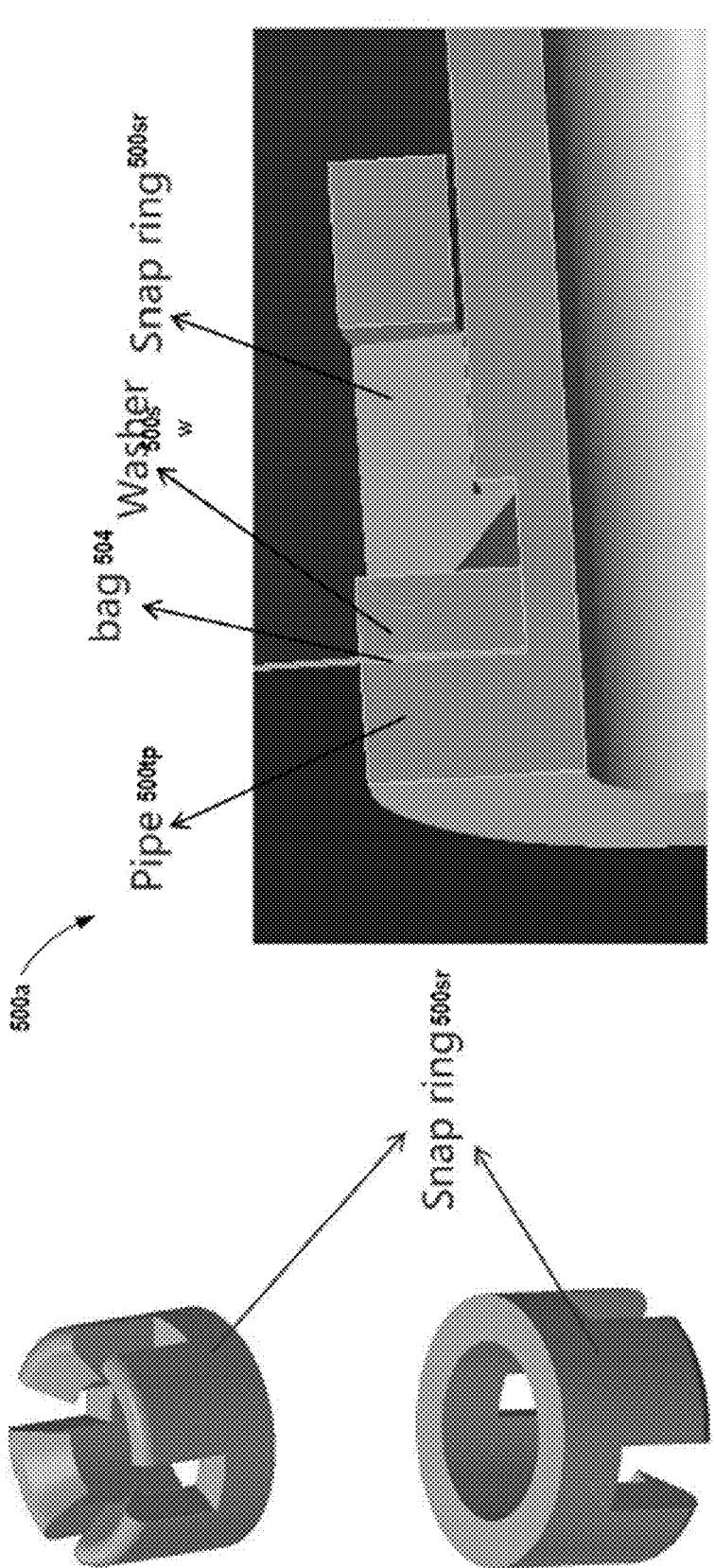

FIGS. 5A-5B show an exemplary inlet and outlet pipe assembly of a sample collection bag. An inlet or outlet assembly $500a$ can comprise a threaded pipe $500tp$, a sealing washer $500sw$, and a snap ring $500sr$. The threaded pipe $500tp$ can comprise an opening $500o$. The threaded pipe $500tp$ can be attached to a hole of a gaseous sample collection bag $504$ by the sealing washer $500sw$ and the snap ring $500sr$ as illustrated in FIG. 5B. The inlet or outlet assembly $500$ can comprise a cap $500c$ (e.g., a polycarbonate cap) for preventing the gaseous sample to enter or exit the gaseous sample collection bag in some configurations.

The opening of the threaded pipe can be round or oval in shape. A dimension (e.g., the radius, the diameter, or the circumference) of the opening of the threaded pipe can be different in different embodiments. In some embodiments, a dimension of the opening of the threaded pipe, is, or is about, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, or a number or a range between any of these values. In some embodiments, a dimension of the opening of the threaded pipe is at least, is at least about, is at most, or is at most about, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, or 25 mm. In some embodiments, a dimension of the opening of the threaded pipe is, or is about, 0.1 in, 0.2 in, 0.3 in, 0.4 in, 0.5 in, 0.6 in, 0.7 in, 0.8 in, 0.9 in, 1 in, or a number or a range between any of these values. In some embodiments, a dimension of the opening of the threaded pipe is at least, is at least about, is at most, or is at most about, 0.1 in, 0.2 in, 0.3 in, 0.4 in, 0.5 in, 0.6 in, 0.7 in, 0.8 in, 0.9 in, or 1 in.

Sample Capturing Tubes

In some embodiments, each of the one or more gaseous sample capturing tubes comprises a first tube opening, for attaching to one of the one or more device inlets, and a second tube opening, for attaching to a bag outlet of one or more bag outlets of the gaseous sample collection bag. In some embodiments, the one or more gaseous sample capturing tubes comprise one or more thermal desorption tubes.

Sample

In some embodiments, the gaseous sample comprises one or more volatile organic compounds (VOCs). One or more of the VOCs of the content in the gaseous sample collection bag, or a portion thereof, collected can be captured onto the one or more gaseous sample capturing tubes.

In some embodiments, a VOC comprises a $C_1$-$C_3$ aldehyde, a $C_1$-$C_3$ alcohol, and/or a $C_2$-$C_{10}$ alkane, wherein a first carbon atom is substituted with the $=O$ group and a second carbon atom is substituted with an —OH group, or an analogue or derivative thereof, in the bodily sample from the test subject. A VOC can comprise a $C_1$-$C_{20}$ alkane, a $C_4$-$C_{10}$ alcohol, a $C_1$-$C_6$ carboxylic acid, and/or a $C_4$-$C_{20}$ aldehyde, or an analogue or derivative thereof. In some embodiments, a VOC comprises a $C_1$-$C_3$ aldehyde, a $C_1$-$C_3$ alcohol, a $C_2$-$C_{10}$ alkane, wherein a first carbon atom is substituted with the $=O$ group and a second carbon atom is substituted with an —OH group, or an analogue or derivative thereof. A VOC can comprise a $C_1$-$C_{20}$ alkane, a $C_4$-$C_{10}$ alcohol, a $C_1$-$C_6$ carboxylic acid, and a $C_4$-$C_{20}$ aldehyde, or an analogue or derivative thereof.

In some embodiments, a VOC comprises formaldehyde, methanol, isopropyl alcohol or acetoin, or a decrease in the concentration of pentane, n-hexane, 1-butanol, propanoic acid, octanal, nonanal, decanal, undecanal, tetradecane, an analogue of any of the proceeding, a derivative of any of the proceeding, or a combination thereof. A VOC can comprise alcohols, ketones, aromatics, organic acids, and/or gases (such as CO, $CO_2$, NO, $NO_2$, $H_2S$, $SO_2$, $CH_4$).

In some embodiments, a VOC comprises a $C_1$-$C_3$ aldehyde. In some embodiments, a VOC comprises a $C_1$, $C_2$ or $C_3$ aldehyde. In some embodiments, a VOC comprises a $C_1$ aldehyde, i.e. formaldehyde. In some embodiments, a VOC comprises a $C_1$-$C_3$ alcohol. In some embodiments, a VOC comprises a $C_1$, $C_2$ or $C_3$ alcohol. In some embodiments, a VOC comprises a $C_1$ alcohol (i.e. methanol) or a $C_3$ alcohol (i.e. isopropyl alcohol).

In some embodiments, a VOC comprises a $C_2$-$C_{10}$ alkane, wherein a first carbon atom is substituted with the $=O$ group and a second carbon atom is substituted with an —OH group. In some embodiments, a VOC comprises a $C_1$, $C_2$, $C_3$, $C_4$, $C_5$, $C_6$, $C_7$, $C_8$, $C_9$, or $C_{10}$, wherein a first carbon atom is substituted with the $=O$ group and a second carbon atom is substituted with an —OH group. In some embodiments, the carbon atom substituted with the $=O$ group is not a terminal carbon atom. In some embodiments, a VOC comprises a $C_3$-$C_6$ alkane. In some embodiments, a VOC comprises a $C_4$ alkane, wherein a first carbon atom is substituted with the $=O$ group, and a second carbon atom is substituted with an —OH group, i.e. acetoin.

In some embodiments, a VOC comprises a $C_1$-$C_{20}$ alkane. In some embodiments, a VOC comprises a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkane. In some embodiments, a VOC comprises a $C_3$-$C_{15}$ alkane. In some embodiments, a VOC comprises a $C_5$-$C_{14}$ alcohol. For example, a VOC comprises a $C_5$ alcohol, i.e. pentane. In some embodiments, a VOC comprises a $C_6$ alcohol, i.e. hexane. In some embodiments, a VOC comprises a $C_{14}$ alcohol, i.e. tetradecane.

In some embodiments, a VOC comprises a $C_4$-$C_{10}$ alcohol. In some embodiments, a VOC comprises a $C_4$, $C_5$, $C_6$, $C_7$, $C_8$, $C_9$, $C_{10}$ alcohol. In some embodiments, a VOC comprises a $C_4$-$C_7$ alcohol, most preferably a $C_4$ alcohol, i.e. butanol.

In some embodiments, a VOC comprises a $C_1$-$C_6$ carboxylic acid. In some embodiments, a VOC comprises a $C_1$, $C_2$, $C_3$, $C_4$, $C_5$, or $C_6$ carboxylic acid. In some embodiments, a VOC comprises a $C_2$-$C_4$ carboxylic acid. In some embodiments, a VOC comprises a $C_3$ carboxylic acid, i.e. propanoic acid.

In some embodiments, a VOC comprises a $C_4$-$C_{20}$ aldehyde. In some embodiments, a VOC comprises a $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ aldehyde. In some embodiments, a VOC comprises a $C_5$-$C_{15}$ aldehyde. In some embodiments, a VOC comprises a $C_7$-$C_{13}$ aldehyde. In some embodiments, a VOC comprises a $C_8$ aldehyde, i.e. octanal. In some embodiments, a VOC comprises a $C_9$ aldehyde, i.e. nonanal. In some embodiments, a VOC comprises a $C_{10}$ aldehyde, i.e. decanal. In some embodiments, a VOC comprises a $C_{11}$ aldehyde, i.e. undecanal.

In some embodiments, the gaseous sample comprises a breath sample of a subject. Causing the display to show the message requesting the gaseous sample to be collected through the bag inlet of the gaseous sample collection bag for the gaseous sample collection duration can comprise causing the display to show a message requesting a subject to breath into the bag inlet of the gaseous sample collection bag for the gaseous sample collection duration.

In some embodiments, a VOC can comprise formaldehyde, methanol, pentane, isopropyl alcohol, n-hexane, 1-butanol, acetoin, propanoic acid, octanal, nonanal, decanal, undecanal, tetradecane, or a combination thereof.

In some embodiments, the gaseous sample comprises an air sample. Causing the display to show the message requesting the gaseous sample to be collected through the bag inlet of the gaseous sample collection bag for the gaseous sample collection duration can comprise causing the display to show a message requesting a user to collect the gaseous sample through the bag inlet of the gaseous sample collection bag for the gaseous sample collection duration.

System

Disclosed herein include embodiments of a system for capturing one or more compounds (e.g., volatile organic compounds (VOCs)) in a gaseous sample. In some embodiments, the system comprises: a device for capturing one or more compounds a gaseous sample of the present disclosure; and an external power source. The system can comprise: instructions for operating the device.

Volatile Organic Compound Capturing Method

Disclosed herein include embodiments of a method for capturing volatile organic compounds (VOCs) using an electric pump device, such as the device 300 described with reference to FIGS. 3A-3B. In some embodiments, the method comprises using an electric pump device for capturing VOCs or a system comprising the electric pump device for capturing VOCs.

FIG. 6 is a flow diagram showing an exemplary method 600 of capturing volatile organic compounds. The method 600 may be embodied in a set of executable program instructions stored on a machine-readable medium, such as one or more disk drives, of an electronic device comprising an electric pump. For example, the device 300 shown in FIGS. 3A-3B and described in greater detail above can execute a set of executable program instructions to implement the method 600. When the method 600 is initiated, the executable program instructions can be loaded into memory, such as RAM, and executed by one or more processors (e.g., a microcontroller) of the device 300. Although the method 600 is described with respect to the device 300 shown in FIGS. 3A-3B, the description is illustrative only and is not intended to be limiting. In some embodiments, the method 600 or portions thereof may be performed serially or in parallel by multiple computing systems.

After the method 600 begins at block 604, the method 600 proceeds to block 608, where an electric pump device for capturing VOCs (e.g., the device 300 for capturing VOCs described with reference to FIGS. 3A-3B) displays a default VOC capturing flow rate and a default VOC capturing duration. The method 600 proceeds from block 608 to block 612, where the electric pump device receives a selected VOC capturing flow rate and a selected VOC capturing duration. If the electric pump device does not receive a user selected VOC capturing flow rate and/or a user selected VOC capturing duration after a default time period (e.g., 5 seconds, 10 seconds, 15 seconds, 20 seconds, or more), the electronic pump device can use the default VOC capturing flow rate as the selected VOC capturing flow rate and/or the default VOC capturing duration as the selected VOC capturing duration Prior to or after block 604, the electric pump device can display a message for any VOC capturing tube attached to the one or more device inlets to be detached from the one or more device inlets. The electric pump device can receive an input to proceed. The electric pump device can activate the electric pump at a purging flow rate for a purging duration. The electric pump device can display a countdown of the purging duration remaining.

Prior to or after block 604, the electric pump device can generate sample identification information. The electric pump device can display the sample identification information. The electric pump device can receive an input to proceed. Alternatively or additionally, the electric pump device can display a message requesting a sample identification information. The electric pump device can receive the sample identification information.

The method 600 proceeds from block 612 to block 616, where the electric pump device displays a message to attach one or more VOC capturing tubes to one or more device inlets of the electronic pump device for capturing one or more VOCs and a VOC collection bag. The electronic pump device can receive an input to proceed.

The electronic pump device can display a message requesting a VOC sample (e.g., a patient's VOC sample or a subject's VOC sample) to be collected through a bag inlet of the VOC sample collection bag for a VOC collection duration. The electronic pump device and display a message requesting a subject to breath into the bag inlet of the VOC collection bag for the VOC collection duration. The electronic pump device can display a countdown of the VOC collection duration remaining. The VOC sample can comprise a breath sample collected from a subject or a patient. The VOC sample can comprise an environmental VOC sample.

The method 600 proceeds from block 616 to block 620, where the electric pump device activates an electric pump of the device to transfer the content in the VOC collection bag through the one or more VOC capturing tubes, into the device via the one or more device inlets and out of the device via a device outlet, at the selected capturing flow rate for the selected capturing duration, thereby one or more VOCs of the content in the VOC collection bag are captured onto the one or more VOC capturing tubes.

The electronic pump device can, when activating the electric pump to transfer the VOC(s) in the content of the VOC collection bag through the one or more VOC capturing tubes, receive sensor information from one or more sensors of the electronic pump device. The electronic pump device can display the sensor information, or a portion thereof. The electronic pump device can generate a linkage relationship of the sensor information and the sample identification information. The electronic pump device can store the sensor information, or a portion thereof, the sample identification information, and/or the linkage relationship in the non-transitory memory and/or a removable memory of the electronic pump device. Alternatively or additionally, the electronic pump device can transmit the sensor information, or a portion thereof, the sample identification information, and/or the linkage relationship to a computing device, such as a remote computing device or a cloud computing device for storing sensor information, or a portion thereof, sample identification information, and/or linkage relationships of samples captured using the electronic pump device and/or other electronic pump devices.

The method 600 ends at block 624.

ADDITIONAL CONSIDERATIONS

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

One skilled in the art will appreciate that, for this and other processes and methods disclosed herein, the functions performed in the processes and methods can be implemented in differing order. Furthermore, the outlined steps and operations are only provided as examples, and some of the steps and operations can be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Accordingly, phrases such as "a device configured to" are intended to include one or more recited devices. Such one or more recited devices can also be collectively configured to carry out the stated recitations. For example, "a processor configured to carry out recitations A, B and C can include a first processor configured to carry out recitation A and working in conjunction with a second processor configured to carry out recitations B and C. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc."

is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

It will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

CLAUSES

1. A device for capturing one or more compounds in a gaseous sample comprising:

one or more device inlets for attaching one or more gaseous sample capturing tubes;
a device outlet;
an electric pump connected to the one or more device inlets for drawing a gaseous sample, or a portion thereof, through the one or more device inlets and expelling the content of the gaseous sample, or a portion thereof, through the device outlet;
one or more sensors connected to the device inlets, the electric pump, and/or the device outlet via one or more air tubes;
a display;
non-transitory memory configured to store executable instructions; and
a microcontroller in communication with the electric pump, the one or more sensors, the display, and the non-transitory memory, the microcontroller programmed by the executable instructions to perform:
causing the display to show a default gaseous sample capturing flow rate and a default gaseous sample capturing duration;
receiving a selected gaseous sample capturing flow rate and a selected gaseous sample capturing duration;
causing the display to show a message to attach one or more gaseous sample capturing tubes to the one or more device inlets and a gaseous sample collection bag;
receiving an input to proceed;
causing the display to show a message requesting a gaseous sample to be collected through a bag inlet of the gaseous sample collection bag for a gaseous sample collection duration;
showing on the display a countdown of the gaseous sample collection duration remaining; and
activating the electric pump to transfer the content in the gaseous sample collection bag, or a portion thereof, through the one or more gaseous sample capturing tubes, into the device via the one or more device inlets and out of the device via the device outlet, at the selected gaseous sample capturing flow rate for the selected gaseous sample capturing duration, thereby one or more compounds of the content in the gaseous sample collection bag, or a portion thereof, collected are captured onto the one or more gaseous sample capturing tubes.

2. The device of clause 1, wherein the gaseous sample comprises one or more volatile organic compounds (VOCs), thereby one or more of the VOCs of the content in the gaseous sample collection bag, or a portion thereof, collected are captured onto the one or more gaseous sample capturing tubes.

3. The device of any one of clauses 1-2, wherein the gaseous sample comprises a breath sample of a subject.

4. The device of any one of clauses 1-3, wherein causing the display to show the message requesting the gaseous sample to be collected through the bag inlet of the gaseous sample collection bag for the gaseous sample collection duration comprises causing the display to show a message requesting a subject to breath into the bag inlet of the gaseous sample collection bag for the gaseous sample collection duration.

5. The device of any one of clauses 1-2, wherein the gaseous sample comprises an air sample.

6. The device of any one of clauses 1-5, wherein at least one of the one or more sensors is connected to the electric bump and the device outlet via at least one of the one or more air tubes.

7. The device of any one of clauses 1-6, wherein at least one of the one or more sensors is connected to at least one of the one or more device inlets and the electric bump via at least one of the one or more air tubes.

8. The device of any one of clauses 1-7, wherein the device comprises: one or more valves in communication with the microcontroller, wherein each of the one or more valves in an opened state allows the gaseous sample to enter into the device via one or more of the one or more device inlets the valve controls, and wherein each of the one or more valves in a closed state prevents the gaseous sample from entering into the device via one or more of the one or more device inlets the valve controls.

9. The device of clause 8, wherein the one or more valves are in the closed state when the microcontroller is programmed by the executable instructions to perform: causing the display to show the message requesting the gaseous sample to be collected through the bag inlet of the gaseous sample collection bag for the gaseous sample collection duration.

10. The device of any one of clauses 1-9, wherein causing the display to show the message to attach the one or more gaseous sample capturing tubes to the one or more device inlets and the gaseous sample collection bag comprises: causing the display to show the message to attach a first tube opening of each of one or more gaseous sample capturing tubes to a different device inlet of the one or more device inlets and attach a second tube opening of each of the one or more gaseous sample capturing tubes to a different bag outlet of one or more bag outlets of the gaseous sample collection bag.

11. The device of any one of clauses 1-10, wherein each of the one or more gaseous sample capturing tubes comprises a first tube opening, for attaching to one of the one or more device inlets, and a second tube opening, for attaching to a bag outlet of one or more bag outlets of the gaseous sample collection bag.

12. The device of any one of clauses 10-11, wherein one, or each, of the one or more bag outlets is perpendicular to the bag inlet.

13. The device of any one of clauses 10-12,
wherein the gaseous sample collection bag comprises a bag body,
wherein the bag inlet comprises an inlet assembly comprising a threaded inlet pipe, an inlet sealing washer, and an inlet snap ring, wherein the threaded inlet pipe is attached to an inlet hole of the bag body by the inlet sealing washer and the inlet snap ring,
wherein each of the one or more bag outlets comprises an outlet assembly comprising a threaded outlet pipe, an outlet sealing washer, and an outlet snap ring, and wherein the threaded outlet pipe is attached to an outlet hole of the bag body by the outlet sealing washer and the outlet snap ring,
optionally wherein the inlet assembly comprises an inlet cap for preventing the gaseous sample to enter or exit the gaseous sample collection bag, and
optionally wherein the outlet assembly comprises an outlet cap for preventing the gaseous sample to enter or exit the gaseous sample collection bag.

14. The device of any one of clauses 10-13, wherein the one or more bag outlets are identical, wherein the one or more bag outlets are next to each other, wherein the one or more bag outlets and the bag inlet are identical, wherein the one or more device inlets are identical, and/or wherein the one or more device inlets are next to each other.

15. The device of any one of clauses 1-14, wherein the one or more gaseous sample capturing tubes comprise one or more thermal desorption tubes.

16. The device of any one of clauses 1-15, wherein the microcontroller is programmed by the executable instructions to perform:
causing the display to show a message for any gaseous sample capturing tube attached to the one or more device inlets to be detached from the one or more device inlets;
receiving an input to proceed;
activating the electric pump at a purging flow rate for a purging duration; and
showing on the display a countdown of the purging duration remaining.

17. The device of any one of clauses 1-16, wherein the microcontroller is programmed by the executable instructions to perform:
generating sample identification information;
causing the display to show the sample identification information; and
receiving an input to proceed.

18. The device of any one of clauses 1-16, wherein the microcontroller is programmed by the executable instructions to perform:
causing the display to show a message requesting sample identification information; and
receiving the sample identification information.

19. The device of any one of clauses 1-18, wherein the microcontroller is programmed by the executable instructions to perform: activating the electric pump to transfer the content in the gaseous sample collection bag through the one or more gaseous sample capturing tubes;
receiving sensor information from the one or more sensors; and
showing on the display the sensor information, or a portion thereof.

20. The device of clause 19, wherein the microcontroller is programmed by the executable instructions to perform:
generating a linkage relationship of the sensor information and the sample identification information;
storing the sensor information, or a portion thereof, the sample identification information, and/or the linkage relationship in the non-transitory memory and/or a removable memory; and/or
transmitting the sensor information, or a portion thereof, the sample identification information, and/or the linkage relationship to a computing device.

21. The device of any one of clauses 1-20,
wherein the default gaseous sample capturing flow rate is about 5 ml/minute to about 2000 ml/minute,
wherein the selected gaseous sample capturing flow rate is about 5 ml/minute to about 2000 ml/minute, and/or
wherein the purging flow rate is about 5 ml/minute to about 2000 ml/minute.

22. The device of any one of clauses 1-21,
wherein the default gaseous sample capturing duration is about 1 minute to about 5 minutes,
wherein the selected gaseous sample capturing duration is about 1 minute to about 5 minutes, and/or
wherein the purging duration is about 10 seconds to 60 seconds.

23. The device of any one of clauses 1-22, wherein volume of the gaseous sample collected in the gaseous sample collection bag is about 2.5 liters, and/or wherein the volume of the gaseous sample collected in the gaseous sample collection bag that passes through the one or more gaseous sample capturing tubes is about 2 liters.

24. The device of any one of clauses 1-23, wherein the gaseous sample collection duration is about 5 seconds to 20 seconds.

25. The device of any one of clauses 1-24, wherein the volume of gaseous sample collected in the gaseous sample collection bag during the gaseous sample collection duration is expected to be about 2.5 liters.

26. The device of any one of clauses 8-25, wherein the one or more valves comprise one or more solenoid valves.

27. The device of any one of clauses 8-26, wherein each of the one or more valves is connected to a different device outlet of the one or more device outlets.

28. The device of any one of clauses 1-27, wherein one, or each of the one or more of the air tubes is rigid, semi-rigid, or elastic.

29. The device of any one of clauses 1-27, wherein a material of one, or each, of the one or more air tubes is latex, rubber, silicone, or a combination thereof.

30. The device of any one of clauses 1-29, wherein sensors of the one or more sensors are connected sequentially.

31. The device of any one of clauses 1-30, wherein each sensor of the one or more sensors is connected to another sensor of the one or more sensors.

32. The device of any one of clauses 1-31, wherein each sensor of the one or more sensors other than a sensor connected to the electric pump and a sensor connected to the device outlet is connected to two sensors of the one or more sensors.

33. The device of any one of clauses 1-32, wherein the one or more sensors comprises a flow rate sensor, a temperature sensor, a pressure sensor, a carbon dioxide ($CO_2$) sensor, a volatile organic compound (VOC) sensor, a humidity sensor, or a combination thereof.

34. The device of any one of clauses 1-32, wherein a sensor connected to the electric pump comprises a flow rate sensor.

35. The device of any one of clauses 1-34, wherein the display comprises a dot matrix display.

36. The device of any one of clauses 1-34, wherein the display comprises a touch screen display for receiving inputs.

37. The device of any one of clauses 1-36, comprising: one or more input keys for receiving inputs.

38. The device of clause 37, wherein the one or more input keys comprise one or more membrane keys.

39. The device of any one of clauses 1-38, comprising:
   a battery connected to the microcontroller for powering the microcontroller;
   a power circuit connected to the battery for charging the battery, optionally wherein the power circuit is connected to the microcontroller for powering the microcontroller; and
   a power inlet connected to the power circuit for connecting the power circuit to an external power source.

40. A system for capturing one or more compounds in a gaseous sample comprising:
   the device of any one of clauses 1-39; and
   an external power source.

41. The system of clause 40, comprising: instructions for operating the device.

42. A method for capturing one or more compounds in a gaseous sample using the device of any one of clauses 1-39 or the system of any one of clauses 40-41.

43. A method for capturing volatile organic compounds (VOCs) comprising:
   displaying a default volatile organic compound (VOC) capturing flow rate and a default VOC capturing duration;
   receiving a selected VOC capturing flow rate and a selected VOC capturing duration;
   displaying a message to attach one or more VOC capturing tubes to one or more device inlets of a device for capturing VOCs and a VOC collection bag;
   receiving an input to proceed;
   activating an electric pump of the device to transfer the content in the VOC collection bag through the one or more VOC capturing tubes, into the device via the one or more device inlets and out of the device via a device outlet, at the selected collection flow rate for the selected capturing duration, thereby one or more VOCs of the content in the VOC collection bag are captured onto the one or more VOC capturing tubes.

44. The method of clause 43, wherein the content of the VOC collection bag comprises a breath sample collected from a patient.

45. The method of clause 43, wherein the content of the VOC collection bag comprises an environmental VOC sample.

46. A gaseous sample collection bag comprising:
   a bag body comprising an inlet hole and one or more outlet holes;
   a bag inlet; and
   one or more bag outlets,
   wherein the bag inlet comprises an inlet assembly comprising a threaded inlet pipe, an inlet sealing washer, and an inlet snap ring, wherein the threaded inlet pipe is attached to the inlet hole of the bag body by the inlet sealing washer and the inlet snap ring, and/or
   wherein each of the one or more bag outlets comprises an outlet assembly comprising a threaded outlet pipe, an outlet sealing washer, and an outlet snap ring, and wherein the threaded outlet pipe is attached to one of the one or more outlet holes of the bag body by the outlet sealing washer and the outlet snap ring.

47. The gaseous sample collection bag of clause 46, wherein the inlet assembly comprises an inlet cap for preventing the gaseous sample to enter or exit the gaseous sample collection bag, and/or wherein the outlet assembly comprises an outlet cap for preventing the gaseous sample to enter or exit the gaseous sample collection bag.

48. The gaseous sample collection bag of any one of clauses 46-47, wherein the one or more bag outlets are identical.

49. The gaseous sample collection bag of any one of clauses 46-48, wherein the one or more bag outlets are next to each other.

50. The gaseous sample collection bag of any one of clauses 46-49, wherein the one or more bag outlets and the bag inlet are identical.

51. The gaseous sample collection bag of any one of clauses 46-50, wherein one, or each, of the one or more outlets holes and/or the inlet is on an edge, or are adjacent to an edge, of the bag body.

52. The gaseous sample collection bag of any one of clauses 46-51, wherein one, or each, of the one or more outlets and/or the inlet are on a diagonal, or adjacent to a diagonal of the bag body.

53. The gaseous sample collection bag of any one of clauses 46-52, wherein one, or each, of the one or more bag outlets is perpendicular, or approximately perpendicular, to the bag inlet.

54. The gaseous sample collection bag of any one of clauses 46-53, wherein one, or each, of the one or more bag outlets and the bag inlet are on different surfaces of the bag body.

55. The gaseous sample collection bag of any one of clauses 46-54, wherein one, or each, of the one or more outlets and the inlet are on an identical surface of the bag body.

56. The gaseous sample collection bag of any one of clauses 46-55, wherein the bag body is rectangular or square in shape when deflated.

57. The gaseous sample collection bag of any one of clauses 46-56, wherein the bag body is heat sealed on three sides.

58. The gaseous sample collection bag of any one of clauses 46-57, wherein the bag body is heat sealed on all sides except one side.

59. The gaseous sample collection bag of any one of clauses 57-58, wherein one, or each, of the sides of the bag body that is heat sealed is impermeable to one or more volatile organic compounds.

60. The gaseous sample collection bag of any one of clauses 46-58, wherein the bag body comprises a sheet folded.

61. The gaseous sample collection bag of any one of clauses 46-60, wherein a material of the bag body comprises high-density polyethylene (HDPE), low-density polyethylene (LDPE), and/or linear low-density polyethylene (LLDPE).

62. The gaseous sample collection bag of any one of clauses 46-61, wherein a material of the bag body is impermeable to one or more volatile organic compound.

What is claimed is:

1. A device for capturing one or more compounds in a gaseous sample comprising:
    one or more device inlets for attaching one or more gaseous sample capturing tubes;
    a device outlet;
    an electric pump connected to the one or more device inlets for drawing a gaseous sample, or a portion thereof, through the one or more device inlets and expelling the content of the gaseous sample, or a portion thereof, through the device outlet;
    one or more sensors connected to the device inlets, the electric pump, and/or the device outlet via one or more air tubes;
    a user interface comprising a display;
    non-transitory memory configured to store executable instructions; and
    a microcontroller in communication with the electric pump, the one or more sensors, the user interface, and the non-transitory memory, the microcontroller programmed by the executable instructions to perform:
        receiving a selected gaseous sample capturing flow rate and a selected gaseous sample capturing duration;
        receiving an input to proceed; and
        activating the electric pump to transfer the content in a gaseous sample collection bag, or a portion thereof, through the one or more gaseous sample capturing tubes, into the device via the one or more device inlets and out of the device via the device outlet, at the selected gaseous sample capturing flow rate for the selected gaseous sample capturing duration, thereby one or more compounds of the content in the gaseous sample collection bag, or a portion thereof, collected are captured onto the one or more gaseous sample capturing tubes,
    wherein the microcontroller is further programmed by the executable instructions to perform:
        causing the display to show a default gaseous sample capturing flow rate and a default gaseous sample capturing duration;
        causing the display to show a message to attach one or more gaseous sample capturing tubes to the one or more device inlets and a gaseous sample collection bag;
        causing the display to show a message requesting a gaseous sample to be collected through a bag inlet of the gaseous sample collection bag for a gaseous sample collection duration; and/or
        showing on the display a countdown of the gaseous sample collection duration remaining, and
    wherein the microcontroller is programmed by the executable instructions to perform:
        activating the electric pump to transfer the content in the gaseous sample collection bag through the one or more gaseous sample capturing tubes;
        receiving sensor information from the one or more sensors; and
        showing on the display the sensor information, or a portion thereof.

2. The device of claim 1,
    wherein the gaseous sample comprises one or more volatile organic compounds (VOCs), thereby one or more of the VOCs of the content in the gaseous sample collection bag, or a portion thereof, collected are captured onto the one or more gaseous sample capturing tubes.

3. The device of claim 1, wherein:
    (i) the gaseous sample comprises a breath sample of a subject, or the gaseous sample comprises an air sample; and/or
    (ii) the device comprises: one or more valves in communication with the microcontroller, wherein each of the one or more valves in an opened state allows the gaseous sample to enter into the device via one or more of the one or more device inlets the valve controls, and wherein each of the one or more valves in a closed state prevents the gaseous sample from entering into the device via one or more of the one or more device inlets the valve controls.

4. The device of claim 1, wherein each of the one or more gaseous sample capturing tubes comprises a first tube opening, for attaching to one of the one or more device inlets, and a second tube opening, for attaching to a bag outlet of one or more bag outlets of the gaseous sample collection bag, optionally wherein one, or each, of the one or more bag outlets is perpendicular to the bag inlet.

5. The device of claim 4,
    wherein the gaseous sample collection bag comprises a bag body,
    wherein the bag inlet comprises an inlet assembly comprising a threaded inlet pipe, an inlet sealing washer, and an inlet snap ring, wherein the threaded inlet pipe is attached to an inlet hole of the bag body by the inlet sealing washer and the inlet snap ring,
    wherein each of the one or more bag outlets comprises an outlet assembly comprising a threaded outlet pipe, an outlet sealing washer, and an outlet snap ring, and wherein the threaded outlet pipe is attached to an outlet hole of the bag body by the outlet sealing washer and the outlet snap ring, optionally wherein the inlet assembly comprises an inlet cap for preventing the gaseous sample to enter or exit the gaseous sample collection bag, and optionally wherein the outlet assembly comprises an outlet cap for preventing the gaseous sample to enter or exit the gaseous sample collection bag.

6. The device of claim 1, wherein the one or more gaseous sample capturing tubes comprise one or more thermal desorption tubes.

7. The device of claim 1, wherein the microcontroller is programmed by the executable instructions to perform:

causing the display to show a message for any gaseous sample capturing tube attached to the one or more device inlets to be detached from the one or more device inlets;

receiving an input to proceed;

activating the electric pump at a purging flow rate for a purging duration; and showing on the display a countdown of the purging duration remaining, and/or wherein:

(i) the microcontroller is programmed by the executable instructions to perform:

generating sample identification information;

causing the display to show the sample identification information; and receiving an input to proceed; or (ii) the microcontroller is programmed by the executable instructions to perform:

causing the display to show a message requesting sample identification information; and receiving the sample identification information.

8. The device of claim 1, wherein the microcontroller is programmed by the executable instructions to perform:

generating a linkage relationship of the sensor information and sample identification information;

storing the sensor information, or a portion thereof, the sample identification information, and/or the linkage relationship in the non-transitory memory and/or a removable memory; and/or transmitting the sensor information, or a portion thereof, the sample identification information, and/or the linkage relationship to a computing device.

9. The device of claim 1, wherein the default gaseous sample capturing flow rate is about 5 ml/minute to about 2000 ml/minute, wherein the selected gaseous sample capturing flow rate is about 5 ml/minute to about 2000 ml/minute, wherein the purging flow rate is about 5 ml/minute to about 2000 ml/minute, wherein the default gaseous sample capturing duration is about 1 minute to about 5 minutes, wherein the selected gaseous sample capturing duration is about 1 minute to about 5 minutes, and/or wherein the purging duration is about 10 seconds to 60 seconds.

10. The device of claim 1, wherein:

(i) the volume of the gaseous sample collected in the gaseous sample collection bag is about 2.5 liters, and/or wherein the volume of the gaseous sample collected in the gaseous sample collection bag that passes through the one or more gaseous sample capturing tubes is about 2 liters;

(ii) the gaseous sample collection duration is about 5 seconds to 20 seconds; and/or (iii) the volume of gaseous sample collected in the gaseous sample collection bag during the gaseous sample collection duration is expected to be about 2.5 liters.

11. The device of claim 3, wherein the one or more valves comprise one or more solenoid valves.

12. The device of claim 1, wherein:

(i) one, or each of the one or more of the air tubes is rigid, semi-rigid, or elastic;

(ii) a material of one, or each, of the one or more air tubes is latex, rubber, silicone, or a combination thereof; and/or (iii) sensors of the one or more sensors are connected sequentially.

13. The device of claim 1, wherein:

(i) each sensor of the one or more sensors, other than a sensor connected to the electric pump and a sensor connected to the device outlet, is connected to two sensors of the one or more sensors;

(ii) the one or more sensors comprises a flow rate sensor, a temperature sensor, a pressure sensor, a carbon dioxide ($CO_2$) sensor, a volatile organic compound (VOC) sensor, a humidity sensor, or a combination thereof; and/or (iii) a sensor connected to the electric pump comprises a flow rate sensor.

14. A method for capturing one or more compounds in a gaseous sample using the device of claim 1.

15. A method for capturing volatile organic compounds (VOCs) comprising:

programming a microcontroller with a set of executable instructions;

displaying a default volatile organic compound (VOC) capturing flow rate and a default VOC capturing duration;

receiving a selected VOC capturing flow rate and a selected VOC capturing duration;

displaying a message to attach one or more VOC capturing tubes to one or more device inlets of a device for capturing VOCs and a VOC collection bag;

receiving an input to proceed; and activating an electric pump of the device to transfer the content in the VOC collection bag through the one or more VOC capturing tubes, into the device via the one or more device inlets and out of the device via a device outlet, at the selected collection flow rate for the selected capturing duration, thereby one or more VOCs of the content in the VOC collection bag are captured onto the one or more VOC capturing tubes, wherein the microcontroller is programmed by the executable instructions to perform:

causing the display to show a message requesting a gaseous sample to be collected through a bag inlet of the VOC collection bag for a gaseous sample collection duration; and/or showing on the display a countdown of the gaseous sample collection duration remaining, and wherein the microcontroller is further programmed by the executable instructions to perform:

activating the electric pump to transfer the content in the VOC collection bag through the one or more VOC capturing tubes;

receiving sensor information from the one or more sensors; and showing on the display the sensor information, or a portion thereof.

16. The method of claim 15, wherein the content of the VOC collection bag comprises a breath sample collected from a patient, or wherein the content of the VOC collection bag comprises an environmental VOC sample.

* * * * *